(12) United States Patent
Iwami et al.

(10) Patent No.: US 11,501,866 B2
(45) Date of Patent: Nov. 15, 2022

(54) MEDICINE VERIFICATION DEVICE AND MEDICINE VERIFICATION METHOD

(71) Applicant: FUJIFILM Toyama Chemical Co., Ltd., Tokyo (JP)

(72) Inventors: Kazuchika Iwami, Ashigarakami-gun (JP); Koji Yokouchi, Ashigarakami-gun (JP)

(73) Assignee: FUJIFILM TOYAMA CHEMICAL CO., LTD., Tokyo (JP)

( * ) Notice: Subject to any disclaimer, the term of this patent is extended or adjusted under 35 U.S.C. 154(b) by 148 days.

(21) Appl. No.: 17/020,090

(22) Filed: Sep. 14, 2020

(65) Prior Publication Data

US 2020/0411158 A1 Dec. 31, 2020

Related U.S. Application Data

(63) Continuation of application No. PCT/JP2019/010230, filed on Mar. 13, 2019.

(30) Foreign Application Priority Data

Mar. 29, 2018 (JP) .............................. JP2018-064342
Feb. 21, 2019 (JP) .............................. JP2019-029362

(51) Int. Cl.
*A61J 3/00* (2006.01)
*G06T 7/00* (2017.01)
(Continued)

(52) U.S. Cl.
CPC ........... *G16H 20/13* (2018.01); *G06K 9/6201* (2013.01); *G06T 7/0014* (2013.01);
(Continued)

(58) Field of Classification Search
None
See application file for complete search history.

(56) References Cited

U.S. PATENT DOCUMENTS 10,064,552 B1 * 9/2018 Vaziri ................. H04N 9/8205
2012/0280075 A1 11/2012 Kim
(Continued)

FOREIGN PATENT DOCUMENTS

CN 102117442 A 7/2011
CN 102768211 A 11/2012
(Continued)

OTHER PUBLICATIONS

International Preliminary Report on Patentability and Written Opinion of the International Searching Authority (Forms PCT/IB/326, PCT/IB/373 and PCT/ISA/237) for International Application No. PCT/JP2019/010230, dated Oct. 8, 2020, with English translation of the Written Opinion.

(Continued)

*Primary Examiner* — Patricia I Young
(74) *Attorney, Agent, or Firm* — Birch, Stewart, Kolasch & Birch, LLP

(57) ABSTRACT

In the present invention, an image of a verification target medicine disposed on an arrangement unit is captured, prescription condition information indicating a prescription condition is acquired, an external force application unit is caused to execute an external force applying operation of applying an external force to the medicine disposed on the arrangement unit to move the medicine when an operation execution condition is satisfied, wherein the operation execution condition includes at least one of: a first operation execution condition that the number of the verification target medicines appearing in the image differs from the quantity of the medicines specified from the prescription condition information; and a second operation execution condition that a shape of the verification target medicine appearing in the (Continued)

image differs from a shape corresponding to a type of the medicine specified from the prescription condition information.

16 Claims, 13 Drawing Sheets

(51) Int. Cl.
G16H 20/13 (2018.01)
H04N 5/247 (2006.01)
G06K 9/62 (2022.01)
H04N 5/225 (2006.01)

(52) U.S. Cl.
CPC ........... *H04N 5/2256* (2013.01); *H04N 5/247* (2013.01); *G05B 2219/39241* (2013.01); *G06T 2207/30242* (2013.01)

(56) References Cited

U.S. PATENT DOCUMENTS

| 2013/0342676 A1 | 12/2013 | Amano et al. |
| 2015/0190312 A1* | 7/2015 | Yuyama ............... G07F 17/0092 |
| | | 700/232 |
| 2016/0104277 A1 | 4/2016 | Takamori |
| 2016/0104282 A1 | 4/2016 | Takahashi |
| 2016/0364868 A1 | 12/2016 | Takahashi |

FOREIGN PATENT DOCUMENTS

| CN | 103596540 A | 2/2014 |
| CN | 105307622 A | 2/2016 |
| CN | 105338945 A | 2/2016 |
| CN | 106061457 A | 10/2016 |
| EP | 2720030 A2 | 4/2014 |
| JP | 2013-144101 A | 7/2013 |
| WO | WO 2012/147907 A1 | 11/2012 |

OTHER PUBLICATIONS

International Search Report (Form PCT/ISA/210) for International Application No. PCT/JP2019/010230, dated May 28, 2019, with English translation.

Extended European Search Report for European Application No. 19777377.3, dated Apr. 26, 2021.

Chinese Office Action and Search Report for corresponding Chinese Application No. 201980022321.2, dated Feb. 9, 2022, with English translation.

* cited by examiner

| TYPE | NAME | IDENTIFICATION INFORMATION | PLAN VIEW SIZE | THICKNESS | MASTER IMAGE |
|---|---|---|---|---|---|
| F1 | NAME F1 | AX | S1(mm) | h1(mm) |  |
| F2 | NAME F2 | BW | S2(mm) | h2(mm) |  |
| F3 | NAME F3 | T | S3(mm) | h3(mm) |  |
| ⋮ | | | | | |

DB

MEDICINE VERIFICATION DEVICE AND MEDICINE VERIFICATION METHOD

CROSS-REFERENCE TO RELATED APPLICATIONS

This application is a Continuation of PCT International Application No. PCT/JP2019/010230 filed on Mar. 13, 2019, which claims priority under 35 U.S.C. § 119(a) to Japanese Patent Application No. 2018-064342 filed on Mar. 29, 2018 and Japanese Patent Application No. 2019-029362 filed on Feb. 21, 2019. Each of the above applications is hereby expressly incorporated by reference, in its entirety, into the present application.

BACKGROUND OF THE INVENTION

The present invention relates to a medicine verification device and a medicine verification method, and more particularly relates to a medicine verification device and a medicine verification method adapted to arrange a verification target medicine on an arrangement unit, capture an image, and verify the type of medicine using the captured image.

As an already known technique, an automatic inspection has been performed by a machine or the like as to whether a medicine is correctly packaged in a packaging bag such as a sachet sheet as instructed by a prescription. Such an automatic inspection device (hereinafter, referred to as a medicine verification device) captures an image of a medicine packed in a packaging bag, for example, within the device. Subsequently, the device verifies the type and number of the medicines appearing in the captured image.

Meanwhile, the accuracy of verification by the medicine verification device is influenced by the position, state, posture, or the like of the medicine when an image is captured. For example, when medicines overlap each other in a packaging bag when an image is captured, it is difficult to correctly specify the number and type of medicines, and this might result in a failure in performing accurate verification. Examples of techniques for resolving such failures include a technique described in JP 2013-144101 A (Patent Literature 1).

The technique described in Patent Literature 1 (refer to claim 1 and FIG. 4 of Patent Literature 1, in particular) includes an inspection part on which an inspection target medicine is disposed, a vibrating means capable of applying vibration to the medicine arranged on the inspection part, an imaging means capable of imaging a medicine disposed on the inspection part, a medicine information detecting means capable of detecting one or both of the quantity and type of the medicine on the basis of an image obtained by the imaging means, and a distribution detecting means that detects distribution of medicines in the inspection part on the basis of the image captured by the imaging means, in which the vibrating means vibrates on the basis of the detection result of the distribution detecting means. According to such a technique, the medicines can be separated and dispersed in a case where the medicines are densely packed in a packaging bag, leading to improvement of verification accuracy.

SUMMARY OF THE INVENTION

As described above, the medicine verification device described in Patent Literature 1 is configured to cause the vibrating means to vibrate according to the distribution of the medicines. However, in view of improving the verification accuracy, when determining whether to move the medicine by vibration or the like, appropriate determination should be made on the basis of not only the distribution state of the medicine, but also on the basis of other situations (for example, the posture of the medicine and imaging conditions).

As described above, in order to improve the accuracy and speed of the verification, there is a need to appropriately set criteria (conditions) for determining as to whether it is necessary to move the medicine.

The present invention has been made in view of the above circumstances and aims to provide a medicine verification device and a medicine verification method capable of appropriately determining whether it is necessary to move a medicine in the verification of the type and the like of a verification target medicine and improving the accuracy and speed of the verification.

In order to achieve the above object, a medicine verification device of the present invention includes: an arrangement unit on which a verification target medicine is disposed; an image capturing unit that captures an image of the verification target medicine disposed on the arrangement unit; a prescription condition information acquisition unit that acquires prescription condition information indicating a prescription condition set for prescribing a medicine; an external force application unit that executes an external force applying operation of applying an external force to the verification target medicine disposed on the arrangement unit to move the verification target medicine; and a control unit that causes the external force application unit to execute the external force applying operation when an operation execution condition is satisfied, wherein the operation execution condition includes at least one of: a first operation execution condition that the number of the verification target medicines appearing in the image differs from the quantity of the medicines specified from the prescription condition information; and a second operation execution condition that a shape of the verification target medicine appearing in the image differs from a shape corresponding to a type of the medicine specified from the prescription condition information.

Note that the "external force applying operation" includes not only a case where an external force is directly applied to the medicine disposed on the arrangement unit, but also a case where the external force is indirectly applied without direct contact with the medicine.

Preferably, the first operation execution condition is that the number of verification target medicines appearing in the image is smaller than the quantity of medicines specified from the prescription condition information.

Preferably, the medicine verification device further includes a light irradiation unit that emits light to the verification target medicine disposed on the arrangement unit when the image capturing unit captures the image, wherein the operation execution condition further includes a third operation execution condition that a plurality of medicines are disposed on the arrangement unit as the verification target medicine and that one medicine and another medicine out of the plurality of medicines are adjacent to each other in an irradiation direction when the light irradiation unit performs light emission.

Preferably, the third operation execution condition is that the plurality of medicines is disposed on the arrangement unit and that the one medicine and the other medicine having a thickness greater than the one medicine are adjacent to each other in the irradiation direction in a state where the other medicine is disposed at a position that blocks light emitted from the light irradiation unit.

Preferably, the light irradiation unit has a plurality of light emitting units and emits light in different directions using the plurality of light emitting units, and when the third operation execution condition is satisfied, the control unit causes the external force application unit to execute the external force applying operation in a case where there exists at least one combination of the one medicine and the other medicine adjacent to each other in the irradiation direction.

Preferably, the operation execution condition further includes a fourth operation execution condition that an arrangement position, within the arrangement unit, of the verification target medicine appearing in the image is a position within a predetermined region.

Preferably, the region is a region separated from the light emitting unit of the light irradiation unit by a distance being a threshold or more in the light irradiation direction.

Preferably, the operation execution condition further includes a fifth operation execution condition that a posture of the verification target medicine appearing in the image is a posture that causes identification information formed on the verification target medicine to be outside an imaging range of the image capturing unit.

Preferably, the image capturing unit includes a plurality of cameras, and the fifth operation execution condition is that the posture of the verification target medicine appearing in the image is a posture that causes the identification information to be outside an imaging range of each of the plurality of cameras.

Preferably, when the fifth operation execution condition is satisfied after causing the external force application unit to execute the external force applying operation, the control unit causes the external force application unit to repeatedly execute the external force applying operation.

Preferably, the verification target medicine is disposed on the arrangement unit in a state of being packed in a light-transmissive packaging bag.

Preferably, the medicine verification device further includes: a conveyance unit that conveys a continuous packaging bag having a strip-like shape including continuously arranged packaging bags, along a conveyance path; and a condition determination unit that determines whether the operation execution condition is satisfied, wherein the arrangement unit is provided at an intermediate position of the conveyance path, the packaging bag in the continuous packaging bag disposed on the arrangement unit is switched by the conveyance of the continuous packaging bag by the conveyance unit, and the image capturing unit captures the image every time the packaging bag disposed on the arrangement unit is switched.

Preferably, in a case that the condition determination unit has determined that the operation execution condition is satisfied, the control unit causes the external force application unit to execute the external force applying operation of applying an external force to the verification target medicine within the packaging bag disposed on the arrangement unit at a time when a result of the determination is obtained by the condition determination unit.

Preferably, the medicine verification device further includes a verification unit that verifies type and the number of the verification target medicines.

Preferably, the verification target medicine is disposed in an unpackaged and exposed state on the arrangement unit.

Preferably, the verification unit reads a master image pre-registered for the type of medicine specified from the prescription condition information and verifies the type of the verification target medicine by using the image captured by the image capturing unit and the master image, and the operation execution condition includes the second operation execution condition, in which the second operation execution condition is that the shape of the verification target medicine appearing in the image captured by the image capturing unit differs from the shape of the medicine appearing in the master image.

Preferably, the external force application unit applies any one of vibration, swing, impact, and pressing force to the verification target medicine disposed on the arrangement unit, as an external force.

In order to achieve the above object, a medicine verification method of the present invention includes: disposing a verification target medicine on an arrangement unit; capturing an image of the verification target medicine disposed on the arrangement unit; acquiring prescription condition information indicating prescription conditions set for prescribing medicines, and causing an external force application unit to execute an external force applying operation of applying an external force to the verification target medicine disposed on the arrangement unit to move the verification target medicine when an operation execution condition is satisfied, wherein the operation execution condition includes at least one of: a first operation execution condition that the number of the verification target medicines appearing in the image differs from the quantity of medicines specified from the prescription condition information; and a second operation execution condition that a shape of the verification target medicine appearing in the image differs from a shape corresponding to a type of the medicine specified from the prescription condition information.

According to the medicine verification device and the medicine verification method of the present invention, it is possible to appropriately determine whether it is necessary to move the medicine in the verification of the type and the like of the verification target medicine. This makes it possible, as a result, to improve the accuracy and speed of the verification of medicines.

DETAILED DESCRIPTION OF THE INVENTION

Hereinafter, a medicine verification device and a medicine verification method of the present invention will be described in detail.

Although the description of the components described below might be made based on typical embodiments of the present invention, the present invention is not limited to such embodiments. That is, the following embodiments are an example provided to facilitate understanding of the medicine verification device and the medicine verification method of the present invention and would not limit the present invention. Accordingly, various improvements or changes may be made without departing from the scope and spirit of the present invention.

In addition, in the present description, a "medicine" represents a solid medicine, and specifically corresponds to a tablet or a capsule.

<<Medicine Prescription Operation>>

Figure 1:
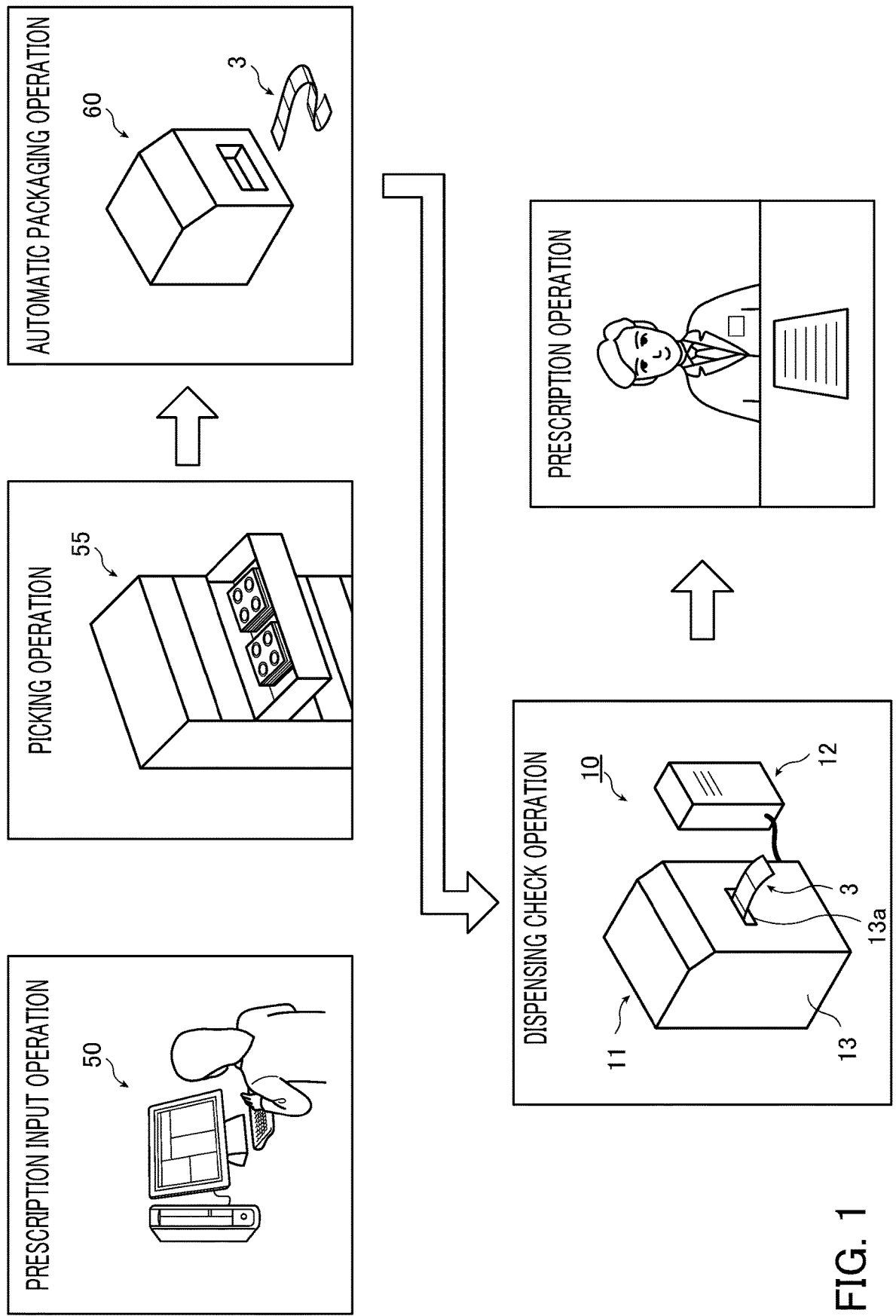
FIG. 1 is a view illustrating a flow of a medicine prescription operation.

Before describing the medicine verification device (hereinafter, a medicine verification device 10) according to one embodiment of the present invention, a medicine prescription operation performed using the medicine verification device 10 will be outlined first. The medicine prescription operation includes operations sequentially performed in the order of a prescription input operation, a picking operation, an automatic packaging operation, a dispensing inspection operation, and a prescription operation, as illustrated in FIG. 1. FIG. 1 is a view illustrating a flow of the medicine prescription operation.

In the prescription input operation, a pharmacist inputs prescription conditions described in a prescription to a computer (hereinafter, prescription condition input device 50). Here, a prescription condition is a condition set for prescribing a medicine to a patient. Examples of input prescription conditions include the name and age of the patient, the type of medicine to be prescribed, the prescription quantity for each of types. The following description assumes that medicines are taken by a plurality of doses and that the prescription quantity for one dose is the same. However, the present invention is not limited to this, and a medicine for only one dose may be prescribed. Furthermore, the type and the prescription quantity of the medicine for one dose may be different each of times.

In the picking operation, on the basis of prescription conditions, a pharmacist picks medicines of the types corresponding to the prescription conditions from a medicine shelf 55 by the quantities according to the prescription conditions. Note that the picking operation is not limited to the case where the pharmacist performs the operation manually, but may be performed automatically by a known automatic picking device on the basis of the prescription conditions input to the prescription condition input device 50.

Furthermore, each of the medicines picked in the present embodiment includes identification information formed on a medicine surface. The "identification information" includes characters, numerals, symbols, or the like for identifying the type of medicine (medicine type) and is formed by engraving or printing. In the present embodiment, it is assumed that identification information is formed on the surface of the medicine by engraving (recess processing). However, the present invention is not limited to the above-described embodiment, and medicines to be picked may include medicines for which identification information is not formed or may include medicines for which identification information is formed by printing.

In the automatic packaging operation, the pharmacist sets the medicines picked in the picking operation onto a tray of a packaging machine 60 illustrated in FIG. 1, and then, the packaging machine 60 automatically packages the medicines in the tray. At this time, the picked medicines are set on a tray for one dose, and the medicines for one dose are packaged in each of the plurality of packaging bags 1. The packaging bag 1 is a known sachet and is formed of a light-transmissive packaging material. Examples of the material of the packaging bag 1 include a laminated film of cellophane and polyethylene, and a polyethylene film.

Figure 2:
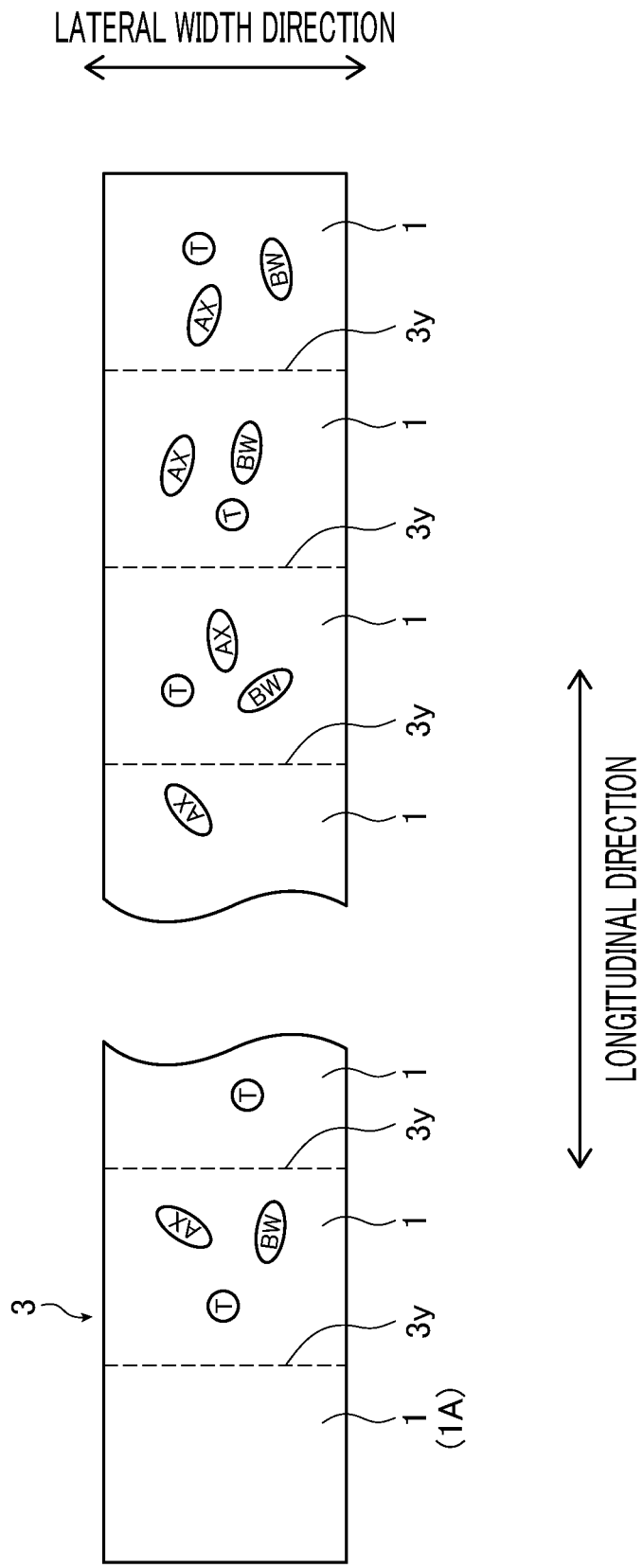
FIG. 2 is a view illustrating a continuous packaging bag.

At a point of completion of the automatic packaging operation, the plurality of packaging bags 1 each containing the medicines are continuously arranged to form a continuous packaging bag 3 having a strip-like shape as illustrated in FIG. 2. At the time of taking the medicine, one packaging bag 1 is separated from the continuous packaging bag 3 and the medicine packed in the separated packaging bag 1 is taken. FIG. 2 is a view illustrating the continuous packaging bag 3.

Note that the plurality of packaging bags 1 are not limited to the form of being continuous as the continuous packaging bag 3 at a point of completion of the automatic packaging operation and may be separated from each other.

At a point of completion of the automatic packaging operation, the packaging bag 1 located at one end of the continuous packaging bag 3 is an empty bag 1A as illustrated in FIG. 2. The empty bag 1A is similar to the packaging bag 1 packing the medicine, except for not containing the medicine inside. The empty bag 1A may be provided at a location other than the end of the continuous packaging bag 3. Moreover, there is no need to include the empty bag 1A in the continuous packaging bag 3.

In the dispensing inspection operation, inspection of whether the prescribed medicine is correct is performed using the medicine verification device 10 illustrated in FIG. 1. Specifically, the operation inspects whether the type and the number (more precisely, the number of each of types) of the medicines contained in each of the packaging bags 1 in the continuous packaging bag 3 is as specified in the prescription.

The prescription operation performs prescription of pre-packaged medicines determined to be correct (as instructed by the prescription) in the dispensing inspection operation, for the patient (prescription destination). At this time, the pharmacist removes the empty bag 1A located at one end of the continuous packaging bag 3 and hands the remaining continuous packaging bag 3 to the patient.

<<Configuration of Medicine Verification Device>>

Next, a configuration of the medicine verification device 10 will be described.

The medicine verification device 10 is used for dispensing inspection and verifies the type and the number (more precisely, the number of each type) of the medicine packed in the packaging bag 1 in the automatic packaging operation. Here, the medicine packed (packaged) in one packaging bag 1 corresponds to the "verification target medicine" of the present invention.

As illustrated in FIG. 1, the medicine verification device 10 includes: a device main body 11 having a function of capturing an image of a medicine as a verification target (specifically, a medicine packed in each of the packaging bags 1); and a processing device 12 having a function of performing dispensing inspection based on the image captured by the device main body 11.

Figure 3:
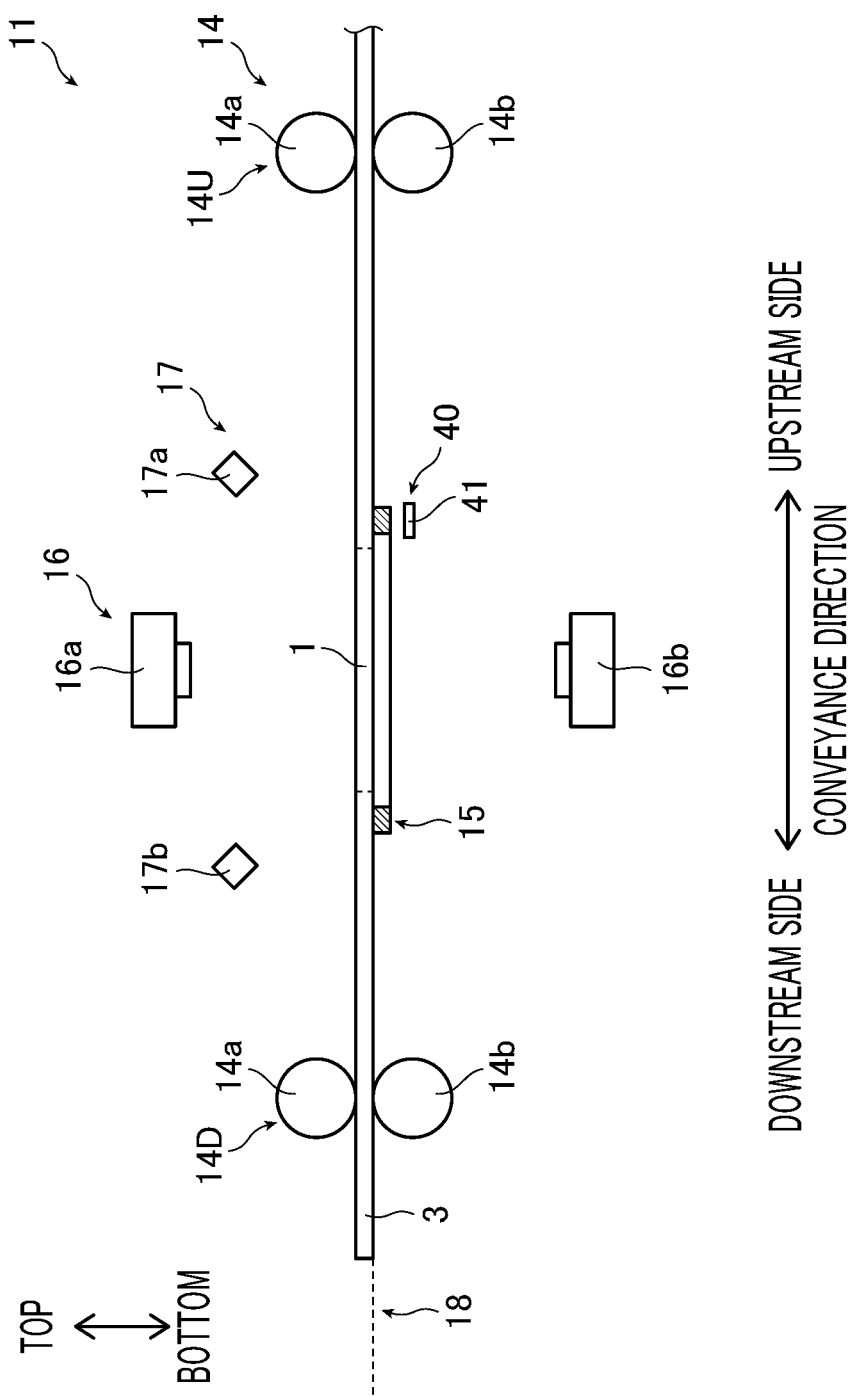
FIG. 3 is a schematic view illustrating an internal structure of a device main body included in the medicine verification device according to one embodiment of the present invention.

The device main body 11 includes a housing 13 illustrated in FIG. 1, and includes, within the housing 13, a conveyance unit 14, an arrangement unit 15, an image capturing unit 16, and a light irradiation unit 17 illustrated in FIG. 3. FIG. 3 is a schematic view illustrating an internal structure of the device main body 11. In addition, the housing 13 of the device main body 11 includes: an introduction part 13a for introducing the continuous packaging bag 3 to the inside of the device main body 11; and a discharge part (not illustrated) for discharging the continuous packaging bag 3 introduced inside the device main body 11 to the outside of the device main body 11.

The conveyance unit 14 has a conveyance path 18 formed inside the device main body 11 and conveys the continuous packaging bag 3 along the conveyance path 18. The continuous packaging bag 3 introduced into the inside of the device main body 11 from the introduction part 13a moves toward the downstream side of the conveyance path 18 by the conveyance operation of the conveyance unit 14 and eventually passes through the discharge part to be discharged to the outside of the device main body 11. Here, the "downstream side" means a side closer to the discharge part in the conveyance direction, and an "upstream side" means a side opposite to the downstream side, that is, a side closer to the introduction part 13a in the conveyance direction.

In the present embodiment, the conveyance path 18 is a horizontal path, and the conveyance unit 14 performs conveyance in a state where a longitudinal direction of the continuous packaging bag 3 runs along the conveyance path 18 (that is, the conveyance direction) and where a thickness direction of the continuous packaging bag 3 runs along the up-down direction (vertical direction).

As illustrated in FIG. 3, the conveyance unit 14 includes an upstream drive unit 14U and a downstream drive unit 14D. The upstream drive unit 14U is arranged on the upstream side of the arrangement unit 15, while the downstream drive unit 14D is arranged on the downstream side of the arrangement unit 15. Each of the upstream drive unit 14U and the downstream drive unit 14D includes a pair of upper and lower nip rollers 14a and 14b, and a motor (not illustrated) that rotationally drives one of the pair of upper and lower nip rollers 14a and 14b. The pair of upper and lower nip rollers 14a and 14b is arranged with a gap enough to allow the continuous packaging bag 3 to pass through, and the rollers rotate in a state of nipping the continuous packaging bag 3 between the rollers. With this configuration, the continuous packaging bag 3 is conveyed in a state where a slight tension is applied.

In the present embodiment, the motor is configured to rotate intermittently. Therefore, the conveyance unit 14 performs the conveyance operation intermittently. In one conveyance operation, the continuous packaging bag 3 moves by a predetermined amount in the conveyance direction. The movement amount (conveyance amount) of the continuous packaging bag 3 in one conveyance operation is set by the control unit 21 of the processing device 12 described below.

Note that the conveyance unit 14 of the present embodiment can perform conveyance to either the upstream side or the downstream side in the conveyance direction by switching the rotational direction of the motor. The conveyance direction is set by the control unit 21 of the processing device 12.

Furthermore, while the present embodiment is an example that applies the conveyance mechanism using the rotation drive of the roller (that is, a roller conveyor), it is also allowable to use other conveyance mechanisms as long as the mechanism can convey the continuous packaging bag 3 properly. For example, it is allowable to apply a belt conveyor that conveys the continuous packaging bag 3 by rotating an endless belt while the continuous packaging bag 3 is mounted on the upper surface of the belt.

Figure 4:
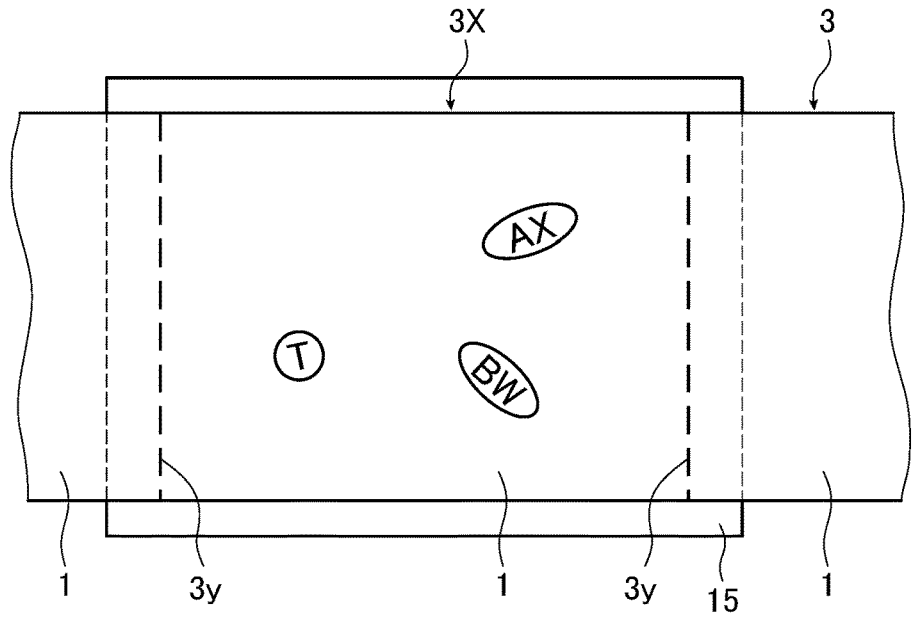
FIG. 4 is a view illustrating an imaging range of an image capturing unit and a part of a continuous packaging bag included in the range.

The arrangement unit 15 is a portion where the verification target medicine is disposed in a state of being packed in the packaging bag 1 and is provided at an intermediate position of the conveyance path 18 as illustrated in FIG. 3. The arrangement unit 15 is a rectangular frame-shaped base and has a size on which one packaging bag 1 can be mounted (for example, a size slightly larger than the outer size of the packaging bag 1 in plan view as illustrated in FIG. 4). In addition, the packaging bags 1 disposed on the arrangement unit 15 in the continuous packaging bag 3 are sequentially switched together with the conveyance of the continuous packaging bag 3 by the conveyance unit 14.

Note that, in a state where the packaging bag 1 is disposed on the arrangement unit 15, the entire region of the upper surface of the packaging bag 1 (the surface facing the upper side of the device main body 11, the similar applies hereinafter) is exposed, while regions other than the edge of the lower surface of the packaging bag 1 (the surface facing the upper side of the device main body 11, the similar applies hereinafter) are exposed. The edge of the packaging bag 1 is a sealed portion formed by stacking and pressing two film sheets constituting the packaging bag 1 together.

The image capturing unit 16 captures an image of the packaging bag 1 disposed on the arrangement unit 15 and an image of the medicine (that is, the verification target medicine) packed in the packaging bag 1. As illustrated in FIG. 3, the image capturing unit 16 includes two cameras, upper and lower, as a plurality of cameras. The camera on the upper side (hereinafter, referred to as a first camera 16a) is disposed immediately above the arrangement unit 15 and captures an image of the medicine packed in the packaging bag 1 disposed on the arrangement unit 15 from above. The lower camera (hereinafter, referred to as a second camera 16b) is disposed immediately below the arrangement unit 15 and captures an image of the medicine packed in the packaging bag 1 disposed in the arrangement unit 15 from below. Here, in the present embodiment, an "image of a medicine" means an image of a medicine captured through the packaging bag 1, that is, an image of a medicine captured in the state of being contained in the packaging bag 1.

In the present embodiment, the conveyance operation by the conveyance unit 14 is to be performed intermittently, and the image capturing unit 16 captures an image of the packaging bag 1 disposed on the arrangement unit 15 and an image of a medicine packed in the packaging bag 1 between the conveyance operations. In addition, every time the packaging bag 1 disposed on the arrangement unit 15 is switched by the conveyance operation, the image capturing unit 16 captures the image of the packaging bag 1 disposed on the arrangement unit 15 and the image of the medicine packed in the packaging bag 1.

In the present embodiment, the imaging range (angle of view) of the first camera 16*a* is set to a rectangular region as illustrated in FIG. 4 (a rectangular region illustrated by a broken line in FIG. 4), which is a range capable of imaging an entire surface of the upper surface of the packaging bag 1 disposed on the arrangement unit 15 and a part (more precisely, an end portion) of the upper surface of the packaging bag 1 located on both sides of the packaging bag 1 disposed on the arrangement unit 15. In other words, the portion of the continuous packaging bag 3 that is within the imaging range of the first camera 16*a* corresponds to an imaging target portion 3*x*, and this portion includes at least a cutout line 3*y* between the packaging bags 1, as illustrated in FIG. 4. Here, the cutout line 3*y* is a boundary recess formed at a boundary position between the packaging bags 1 in the continuous packaging bag 3, and more specifically, is constituted by a dashed linear groove being formed from one end to the other end of the continuous packaging bag 3 in the lateral width direction of the continuous packaging bag 3.

FIG. 4 is a view illustrating an imaging range of the image capturing unit 16 and a part of the continuous packaging bag 3 included in the range.

Similarly, the imaging range (angle of view) of the lower camera 16*b* is set to a rectangular region, which is a range capable of imaging a region on the lower surface of the packaging bag 1 disposed on the arrangement unit 15 that is inside the arrangement unit 15 and is exposed, and a portion (more precisely, an end portion) of the lower surface of the packaging bag 1 located on both sides of the packaging bag 1 disposed on the arrangement unit 15. In other words, the portion of the continuous packaging bag 3 that is within the imaging range of the second camera 16*b* corresponds to the imaging target portion 3*x*, and this portion includes at least the cutout line 3*y* between the packaging bags 1.

The image capturing unit 16 may be any type as long as it as a function of acquiring image data of a subject. Examples of this include a Charge-Coupled Device (CCD) image sensor and a Complementary Metal Oxide Semiconductor (CMOS) image sensor, although the present invention is not limited to these.

Furthermore, the image capturing unit 16 in the present embodiment is implemented by two cameras, but the number of cameras is not particularly limited and may be one, or three or more.

Furthermore, in the present embodiment, the camera is installed at a position vertically sandwiching the arrangement unit 15. However, the installation position of the camera can be set to any position as long as the packaging bag 1 disposed on the arrangement unit 15 and the medicine packed in the packaging bag 1 can be imaged satisfactorily. For example, the camera may be installed only above the arrangement unit 15 or only below the arrangement unit 15.

The light irradiation unit 17 is configured to perform light emission to the packaging bag 1 disposed on the arrangement unit 15 and the medicine packed in the packaging bag 1 (that is, the verification target medicine) when the image capturing unit 16 captures an image. More specifically, the light irradiation unit 17 performs light emission toward a portion (that is, the surface of the imaging target portion 3*x*) within the imaging range of the image capturing unit 16 out of the continuous packaging bag 3.

Figure 5:
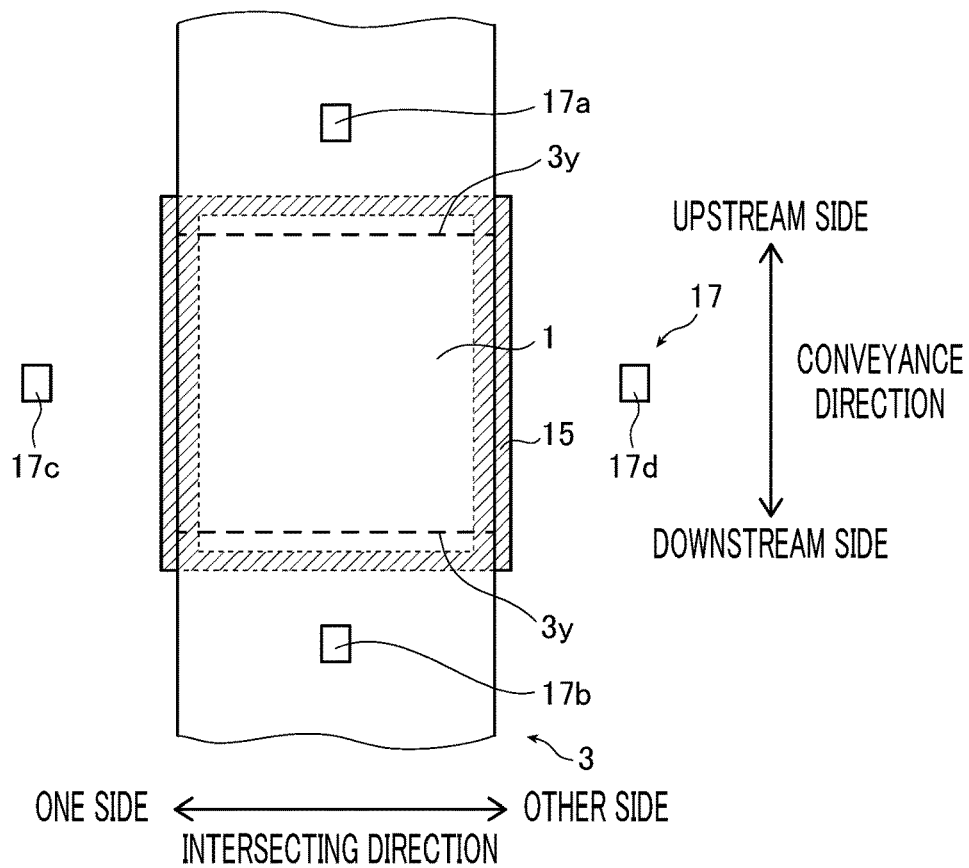
FIG. 5 is a schematic top view of a plurality of light emitting units of the light irradiation unit.

As illustrated in FIG. 5, the light irradiation unit 17 has a plurality of light emitting units, specifically four light emitting units 17*a*, 17*b*, 17*c*, and 17*d* in the present embodiment. FIG. 5 is a schematic top view of a plurality of light emitting units of the light irradiation unit 17. The four light emitting units 17*a*, 17*b*, 17*c*, and 17*d* are light sources used when the light irradiation unit 17 performs light emission, and individually arranged on four sides of the arrangement unit 15 as illustrated in FIG. 5. The light irradiation unit 17 performs light emission in different directions using the four light emitting units 17*a*, 17*b*, 17*c*, and 17*d* (a plurality of light emitting units).

More specifically, the two light emitting units 17*a* and 17*b* are arranged at positions opposite to each other as viewed from the arrangement unit 15 in the conveyance direction, and the units emit light in mutually opposite directions. That is, one light emitting unit 17*a* (hereinafter, referred to as a first light emitting unit 17*a*) emits light from the upstream side in the conveyance direction to the arrangement unit 15 located downstream in the conveyance direction. The other light emitting unit 17*b* (hereinafter, referred to as a second light emitting unit 17*b*) emits light from the downstream side in the conveyance direction to the arrangement unit 15 located upstream in the conveyance direction.

The remaining two light emitting units 17*c* and 17*d* out of the four light emitting units 17*a*, 17*b*, 17*c*, and 17*d* are arranged at positions opposite to each other as viewed from the arrangement unit 15 in a direction (hereinafter, intersecting direction) intersecting the conveyance direction, and the units emit light in mutually opposite directions. That is, one light emitting unit 17*c* (hereinafter, referred to as a third light emitting unit 17*c*) emits light from one side in the intersecting direction toward the arrangement unit 15 on the other side. The other light emitting unit 17*d* (hereinafter, referred to as a fourth light emitting unit 17*d*) emits light to the arrangement unit 15 on one side, from the other side, in the intersecting direction. Here, "one side in the intersecting direction" means, for example, a side near one end of the arrangement unit 15 in the intersecting direction, while "the other side in the intersecting direction" means a side close to the other end of the arrangement unit 15 in the intersecting direction.

The light irradiation unit 17 uses a part or all of the four light emitting units 17*a*, 17*b*, 17*c*, and 17*d* to perform light emission to the packaging bag 1 disposed on the arrangement unit 15 and the medicine packed in the packaging bag 1. At this time, as observed from FIGS. 3 and 5, the light irradiation unit 17 performs light emission diagonally to the packaging bag 1 disposed on the arrangement unit 15 and the medicine (that is, the imaging target portion 3*x*) packed in the packaging bag 1. This direction is advantageous because applying light diagonally to the surface of the medicine can emphasize the contour of the identification information formed on the surface of the medicine (in particular, an edge portion of the contour at the object of light emission).

In addition, in the present embodiment, it is possible to switch the light emitting units 17*a*, 17*b*, 17*c*, and 17*d* used by the light irradiation unit 17 when the image capturing unit 16 captures an image. Specifically, the light irradiation unit 17 performs light emission using one of the four light emitting units 17*a*, 17*b*, 17*c*, and 17*d*. While the light irradiation unit 17 performs light emission from one light emitting unit, the image capturing unit 16 captures an image of the medicine packed in the packaging bag 1 disposed on the arrangement unit 15, by one imaging. Thereafter, the light irradiation unit 17 switches one light emitting unit used immediately before to another light emitting unit among the light emitting units 17a, 17b, 17c, and 17d and then, performs light emission using the light emitting units 17a, 17b, 17c, and 17d after the switching. In the meantime, the image capturing unit 16 captures an image of the medicine packed in the packaging bag 1 disposed on the arrangement unit 15 again.

Thereafter, the light irradiation unit 17 sequentially switches the light emitting units 17a, 17b, 17c, and 17d using the similar procedure, and the image capturing unit 16 captures an image of the medicine packed in the packaging bag 1 disposed on the arrangement unit 15 every time the light irradiation unit 17 switches the light emitting units 17a, 17b, 17c, and 17d. This results in acquisition of captured images for each of the light irradiation directions (that is, four images having mutually different reflection states of light at each of portions of the medicine surface) for the medicine packed in one packaging bag 1 disposed on the arrangement unit 15. However, the present invention is not limited to this, and it is allowable to use a configuration in which two to four of the four light emitting units 17a, 17b, 17c, and 17d are simultaneously turned on, and the light irradiation unit 17 performs light emission toward the medicine packed in one packaging bag 1 disposed on the arrangement unit 15 simultaneously from two to four directions.

The light emitting units 17a, 17b, 17c, and 17d used by the light irradiation unit 17 for light emission may be implemented with known light sources, including any of a point light source, a line light source, or a surface light source. Specifically, examples of applicable light sources include: electroluminescence types such as Light Emitting Diode (LED), semiconductor laser (Laser Diode (LD)), and organic Electro-luminescence (EL), radiant heat types such as halogen bulbs and incandescent bulbs, discharge emission types such as a mercury lamp and a fluorescent lamp, and a combination of these light sources with a light guide member such as a light guide plate or an optical fiber.

Furthermore, the present embodiment uses the light irradiation unit 17 having four light emitting units 17a, 17b, 17c, and 17d. However, the number of light emitting units (light sources) is not particularly limited, and it is sufficient as long as two or more units are provided.

Moreover, instead of arranging the four light emitting units 17a, 17b, 17c, and 17d around the arrangement unit 15, it is allowable to dispose one annular light emitting unit. With such a configuration, it is possible to irradiate the arrangement unit 15 with light from all directions of 360 degrees.

In addition to the parts described above (specifically, the conveyance unit 14, the arrangement unit 15, the image capturing unit 16, and the light irradiation unit 17), the device main body 11 also includes an external force application unit 40 illustrated in FIG. 3. Details of the external force application unit 40 will be described below.

The processing device 12 executes a series of information processing in the implementation of the dispensing inspection. In the present embodiment, the processing device 12 is constituted using a personal computer (PC) external to the device main body 11. However, the present invention is not limited to this, and the processing device 12 may be constituted using a computer built in the device main body 11.

Furthermore, the processing device 12 is communicably connected to the device main body 11, the prescription condition input device 50, and a database server 70 described below. The connection method between the processing device 12 and each device may be a wired connection method or a wireless connection method.

Figure 6:
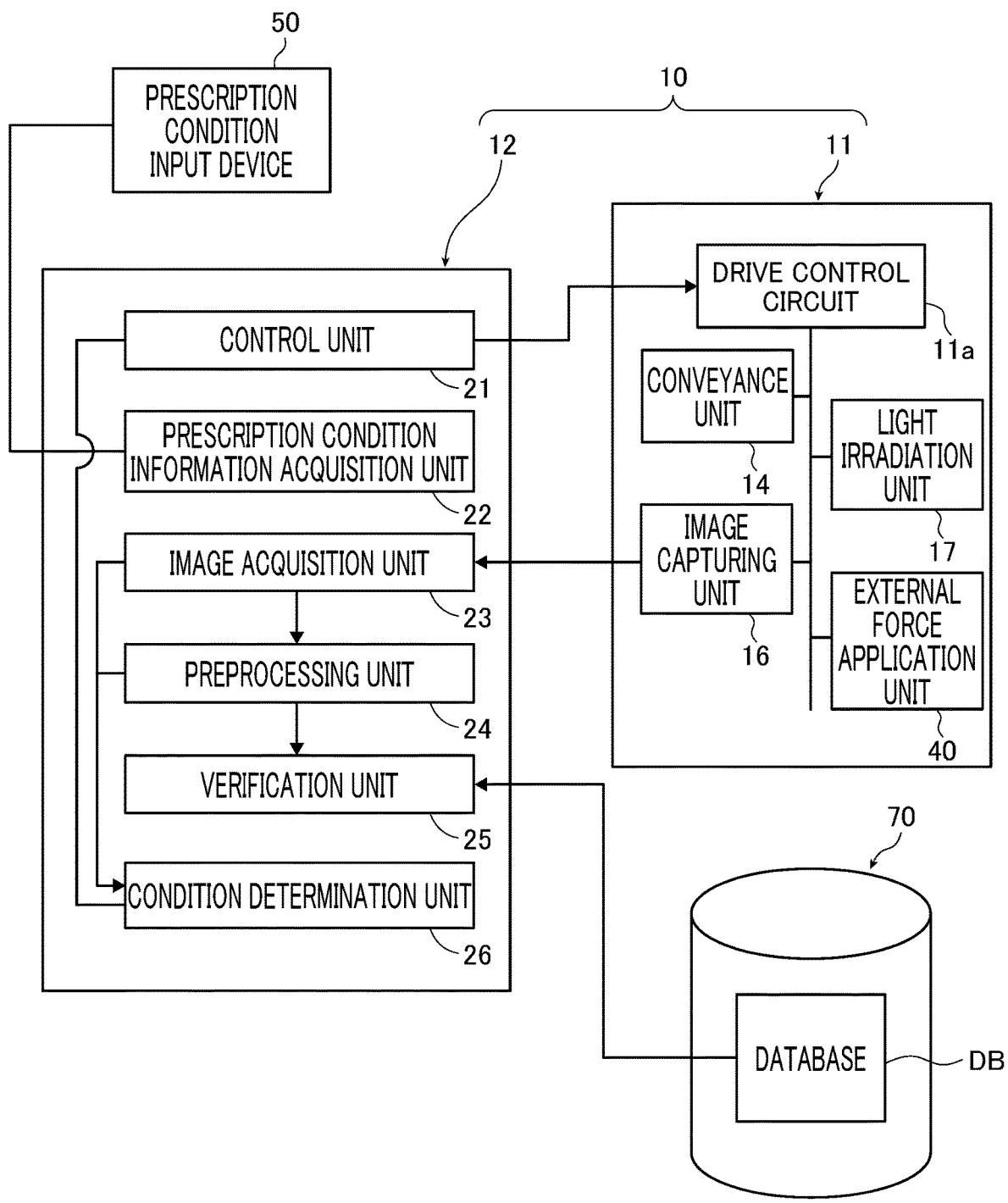
FIG. 6 is a block diagram illustrating a configuration of a processing device included in a medicine verification device according to one embodiment of the present invention.

As illustrated in FIG. 6, the processing device 12 includes the control unit 21, a prescription condition information acquisition unit 22, an image acquisition unit 23, a preprocessing unit 24, a verification unit 25, and a condition determination unit 26. FIG. 6 is a block diagram illustrating a configuration of the processing device 12. These units are implemented by cooperation of hardware devices such as a Central Processing Unit (CPU) and a memory (not illustrated) included in the processing device 12, and an information processing program stored in the processing device 12. The information processing program may be read and obtained from a recording medium such as a Compact Disc Read Only Memory (CD-ROM) storing the program, or may be downloaded and obtained from a predetermined site via a network.

In the present embodiment, individual functional units of the processing device 12 (specifically, the control unit 21, the prescription condition information acquisition unit 22, the image acquisition unit 23, the preprocessing unit 24, the verification unit 25, and the condition determination unit 26) are constituted by one personal computer. However, the present invention is not limited to this, and it is allowable to use a configuration in which a part of the above functional units is constituted by one personal computer while the remaining functional units are constituted by another personal computer.

The control unit 21 is electrically connected to each of units of the device main body 11 (specifically, the conveyance unit 14, the image capturing unit 16, the light irradiation unit 17, and the external force application unit 40) via a drive control circuit 11a mounted on the device main body 11 and controls each of the units of the device main body 11. More specifically, the control unit 21 performs control related to the conveyance operation of the conveyance unit 14, such as controlling a conveyance amount, a conveyance direction, a conveyance operation timing, or the like in one conveyance operation. In addition, the control unit 21 performs control related to the imaging operation of the image capturing unit 16, such as controlling a camera to be used among the two cameras 16a and 16b of the image capturing unit 16, and a timing and the like of imaging. In addition, the control unit 21 performs control related to the light emitting operation of the light irradiation unit 17, such as controlling the light emitting unit to use among the four light emitting units 17a, 17b, 17c, and 17d included in the light irradiation unit 17, and the timing and the like of light emission.

Furthermore, when the operation execution condition is satisfied, the control unit 21 causes the external force application unit 40 to execute an external force applying operation. Here, the external force applying operation is an operation of the external force application unit 40 that applies an external force to the medicine (that is, the verification target medicine) packed in the packaging bag 1 disposed on the arrangement unit 15 to move the medicine. With execution of the external force applying operation of the external force application unit 40, it is possible to spread the medicines when they are densely packed in the packaging bag 1 disposed on the arrangement unit 15, lay down the medicines when they stand upright, or move the medicine when its position is out of a desired range. Note that the external force applying operation includes not only a case where an external force is directly applied to the medicine or the packaging bag 1 disposed on the arrangement unit 15, but also a case where the external force is indirectly applied without direct contact with the medicine or the packaging bag 1.

The operation execution conditions set for determining whether to execute the external force applying operation will be described below in detail.

The prescription condition information acquisition unit 22 is communicably connected to the prescription condition input device 50 and acquires prescription condition information by communicating with the prescription condition input device 50. Here, the prescription condition information is information indicating the prescription condition, which specifically is electronic data indicating the prescription condition input to the prescription condition input device 50 by the pharmacist.

In the present embodiment, when the input of the prescription condition is completed in the prescription condition input device 50, the prescription condition information is automatically transmitted from the prescription condition input device 50 to the prescription condition information acquisition unit 22, and then the prescription condition information acquisition unit 22 receives the above prescription condition information. However, the present invention is not limited to this. It is also allowable to use a configuration in which an information transmission request is transmitted from the prescription condition information acquisition unit 22, and the prescription condition input device 50 transmits the prescription condition information at a point of reception of the request by the prescription condition input device 50. More specifically, character string information or the two-dimensional barcode information for specifying the prescription condition is printed on a tip portion of the continuous packaging bag 3 (a portion of the continuous packaging bag 3 first introduced into the device main body 11). The prescription condition information acquisition unit 22 reads the above-described printed information when the continuous packaging bag 3 is introduced into the device main body 11. Thereafter, based on the read printed information, the prescription condition information acquisition unit 22 requests a prescription condition information indicating prescription conditions related to the medicine packaged in each of the packaging bags 1 of the continuous packaging bag 3 introduced into the device main body 11, against the prescription condition input device 50. After receiving this request, the prescription condition input device 50 analyzes the request, specifies prescription condition information related to the request, and transmits the specified prescription condition information to the processing device 12.

The image acquisition unit 23 is connected to the image capturing unit 16 (more precisely, the first camera 16*a* and the second camera 16*b*) and acquires, via a network, an image captured by the image capturing unit 16. Here, the image acquired by the image acquisition unit 23 corresponds to image data in specifically, Joint Photographic Experts Group (JPEG) format, Graphics Interchange Format (GIF) format, Portable Network Graphics (PNG) format, Tagged Image File Format (TIFF), or Bitmap Image (BMP) format.

Note that the image acquisition unit 23 acquires an image from the image capturing unit 16 each time the image capturing unit 16 captures an image. More specifically, in the present embodiment, as described above, images are captured a plurality of times (specifically, eight times) separately for each of imaging conditions for one packaging bag 1 in which medicines are packaged. Accordingly, the image acquisition unit 23 acquires images for various imaging conditions (that is, eight images) for each of the packaging bags 1 and the medicines packed in each of the packaging bags 1. Furthermore, when the packaging bag 1 disposed on the arrangement unit 15 is switched, the image capturing unit 16 newly captures an image for each of imaging conditions. Accordingly, the image acquisition unit 23 acquires the newly captured image for each of the conditions.

The preprocessing unit 24 performs preprocessing on the image acquired by the image acquisition unit 23 from the image capturing unit 16 (that is, the image data of the verification target medicine). The preprocessing is a process for emphasizing the identification information formed on the surface of the medicine appearing in the image acquired by the image acquisition unit 23.

More specifically, in the present embodiment, as described above, an image is captured a plurality of times (specifically, four times) in various light irradiation directions for the medicine packed in one packaging bag 1. Here, each of the images for each of the light irradiation directions has unevenness in light illuminance occurring on the surface of the medicine appearing in the image. Such uneven illuminance of light has an influence in detecting and specifying identification information formed on the surface of the medicine. Furthermore, the illuminance unevenness of light varies depending on the light irradiation direction. Therefore, the preprocessing unit 24 performs preprocessing. For an image captured for each of light irradiation directions, the preprocessing uses an edge extraction filter in a direction corresponding to the irradiation direction, which is an edge extraction filter of a size corresponding to the number of pixels of an edge (marked groove) of the identification information appearing in each of the images, thereby generating an edge image for each of irradiation directions, and thereafter, generates a combined image in which a plurality of edge images are combined. The edge extraction filter can include at least one of a Sobel filter, a Laplacian filter, and a Canny filter, and can be appropriately selected according to a verification method to be described below.

The image that has undergone the above preprocessing is an image from which the illuminance unevenness of light that varies according to the light irradiation direction is eliminated as much as possible and in which the identification information formed on the surface of the medicine appearing in the image is emphasized. Specifically, it is possible to reduce the information other than the engraving, such as the pattern and the scratches smaller than the groove of engraving indicating the identification information on the surface of the medicine, leading to extraction of the engraving.

The verification unit 25 verifies the number and type of medicines (that is, verification target medicine) packed in the packaging bag 1 disposed on the arrangement unit 15.

Figure 7:
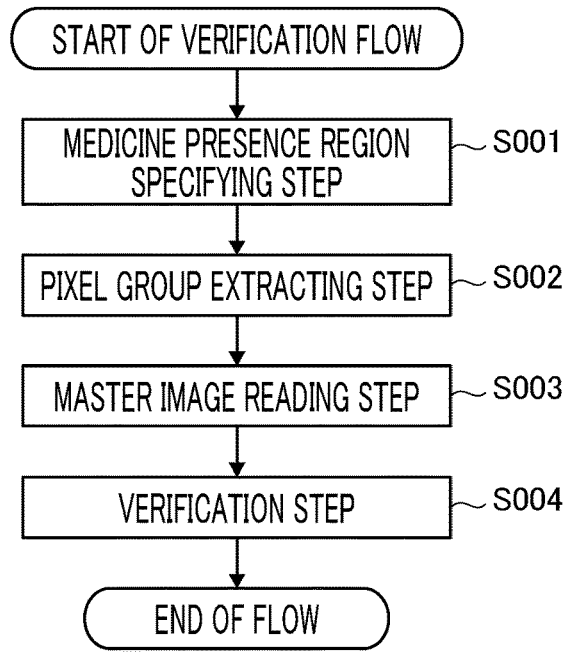
FIG. 7 is a diagram illustrating a general verification flow performed by a verification unit.

The specific procedure of the verification performed by the verification unit 25 will be described with reference to FIG. 7. FIG. 7 is a diagram illustrating a general verification flow performed by the verification unit 25. The verification flow of the verification unit 25, as illustrated in FIG. 7, first performs a step of specifying a region including an image of a verification target medicine from the image on which preprocessing has been performed (S001). Hereinafter, an image on which preprocessing has been performed is referred to as a "preprocessed image", and a region including an image of a medicine in the preprocessed image is referred to as a "medicine presence region".

In the present embodiment, the preprocessing is performed first, and then a medicine presence region specifying step S001 and a pixel group extracting step S002 described below are performed on the preprocessed image obtained by the preprocessing. However, the present invention is not limited to this mode. It is allowable to use a mode in which the medicine presence region specifying step S001 and the pixel group extracting step S002 are performed on each of the captured images obtained for each of light irradiation directions, and then preprocessing is performed on the captured images for each of irradiation directions in which these steps were performed (more precisely, a medicine extraction image X described below).

The medicine presence region specifying step S001 performs a known edge extraction process and a known segmentation process on the preprocessed image to specify a contour of the medicine in the image. Then, a region surrounded by the specified contour is specified as a medicine presence region. In a case where a plurality of medicines are captured in the preprocessed image, the medicine presence regions are specified by the number of medicines.

Figure 8:
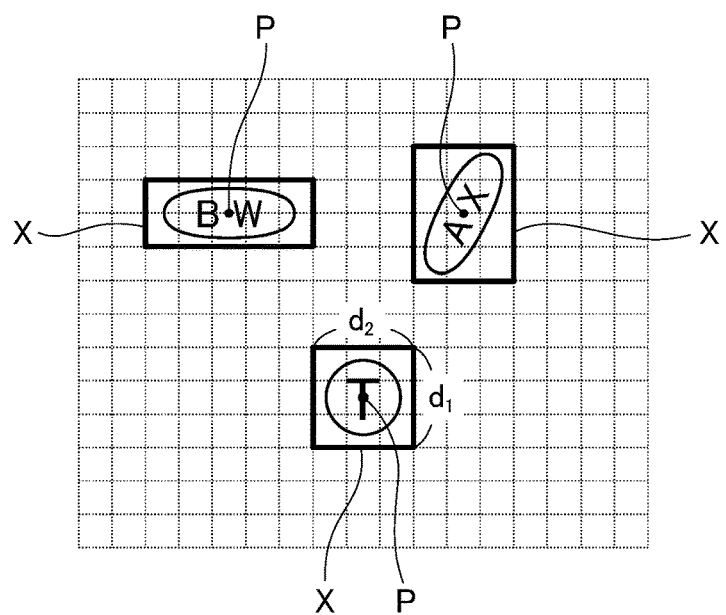
FIG. 8 is a view illustrating a medicine extraction image.

After performing the medicine presence region specifying step S001, the verification unit 25 extracts a pixel group corresponding to the medicine presence region from among the pixel group forming the preprocessed image (S002). As illustrated in FIG. 8, the extracted pixel group forms a rectangle (rectangular region denoted by reference symbol X in FIG. 8) surrounding the medicine presence region. Hereinafter, the extracted pixel group is referred to as a "medicine extraction image X". In a case where a plurality of medicine presence regions are specified in the medicine presence region specifying step S001, the medicine extraction image X is specified for each of medicine presence regions.

FIG. 8 is a view illustrating the medicine extraction image X. Note that the pixel size (single pixel size with respect to the image) illustrated in FIG. 8 is larger than the actual pixel size for the sake of convenience of illustration.

The pixel group extracting step S002 specifies the size and the position of the medicine extraction image X. Here, the size of the medicine extraction image X is the area of a rectangular pixel group forming the medicine extraction image X and corresponds to the product of lengths d1 and d2 of the two sides illustrated in FIG. 8.

Furthermore, the position of the medicine extraction image X is a coordinate position when the reference position is an origin and the conveyance direction and the intersecting direction are defined as coordinate axis directions.

Specifically, this corresponds to an intersecting position of the diagonal lines of the rectangular pixel group forming the medicine extraction image X, namely the coordinates of point P illustrated in FIG. 8. By specifying the position of the medicine extraction image X in this manner, it is possible to specify the imaging position (arrangement position) of the verification target medicine corresponding to the imaging range of the image capturing unit 16 (more precisely, the angle of view of each of the first camera 16a and the second camera 16b). While the present embodiment is a case where the reference position as the origin is set at the center position of the imaging range of the image capturing unit 16 (more precisely, the first camera 16a and the second camera 16b), the position is not limited to this and it may be set at any position.

After execution of the pixel group extracting step S002, the verification unit 25 executes a step of specifying the type of medicine to be prescribed from the prescription condition information acquired using the prescription condition information acquisition unit 22 and then reading a master image of the specified type of medicine from the database DB (S003). In this step S003, in a case where a plurality of types of medicines to be prescribed exist, that is, where a plurality of types of medicines are packaged in the packaging bag 1, a master image is read for each of types.

Here, the master image will be described. The master image is an image of a medicine registered corresponding to the type of medicine and is an image registered in advance for the type of medicine specified from the prescription condition information. Furthermore, in the present embodiment, the master image is obtained from an image of a medicine captured in a state of being packed in the packaging bag 1. In addition, in a case where verification of a type of medicine has been performed by the verification unit 25 in the past, a captured image of the medicine verified to match the type of medicine appearing in the master image, out of the images (more precisely, medicine extraction image X) of the type of medicine captured in the past by the image capturing unit 16, is to be registered as a new master image.

Figure 9:
FIG. 9 is a diagram illustrating a database in which master images are registered.
Figure 9:
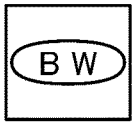
Figure 9:
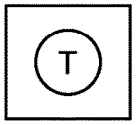

The database DB will be described. As illustrated in FIG. 9, the database DB is a database in which a master image of each of medicines and a type of the medicine are registered in association with each other. FIG. 9 is a diagram illustrating a database DB in which master images are registered.

In addition to the master image, the database DB includes a medicine name, identification information formed on the surface of the medicine, a plan view size and a thickness as medicine size individually registered in association with the type of the medicine. The information registered in the database DB is not limited to the above information, and information other than the above information may be registered.

In the present embodiment, the database DB is provided in a database server 70 externally provided, and the verification unit 25 communicates with the database server 70 to access the database DB. However, the present invention is not limited to this, and the database DB may be provided in the processing device 12, that is, may be stored in a storage medium in the processing device 12.

After reading the master image from the database DB, the verification unit 25 verifies the type of the verification target medicine and the number of each of types (S004) using the read master image and the image of the verification target medicine captured by the image capturing unit 16 (more precisely, the medicine extraction image X).

More specifically, in the verification step S004, template matching with the master image is performed for each of the plurality of medicine extraction images X to evaluate the similarity (correlation value) with the master image. Examples of an applicable similarity evaluation method include a known geometric hashing method or a Locally Likely Arrangement Hashing (LLHA) method. Subsequently, it is verified that the type of medicine captured in the image having the highest similarity among the plurality of medicine extraction images X matches the type of medicine captured in the master image.

By repeating the above procedure for the read master images (that is, for the number of medicine types indicated by the prescription condition information acquired by the prescription condition information acquisition unit 22), the type is specified for each of verification target medicines.

Thereafter, the verification unit 25 totals individually the number of medicines whose types are specified and counts the number of each of types.

The verification is performed by the verification unit 25 using the procedure described above. In addition, when the packaging bag 1 disposed on the arrangement unit 15 is switched (that is, when the verification target medicine changes), the verification is repeated each of times. That is, when the packaging bag 1 disposed on the arrangement unit 15 is switched and an image of the medicine packed in the packaging bag 1 is acquired, verification is performed using the newly acquired image. When the medicines are packaged under the same prescription condition in each of the packaging bags 1 of the continuous packaging bag 3, the master image used in the first verification can be used as it is in the second and subsequent verifications. Accordingly, step S003 of reading a master image from the database DB may be omitted.

With the procedure described above, verification is performed on the medicine packed in each of the packaging bags 1 of the continuous packaging bag 3 (more precisely, the packaging bag 1 other than the empty bag 1A), and thus it is possible to inspect whether the medicine is correctly packaged in each of the packaging bags 1 as instructed by the prescription.

The condition determination unit 26 determines whether the operation execution condition is satisfied. The condition determination unit 26 will be described in detail in a section below.

<<Operation of Medicine Verification Device>>

Figure 10:
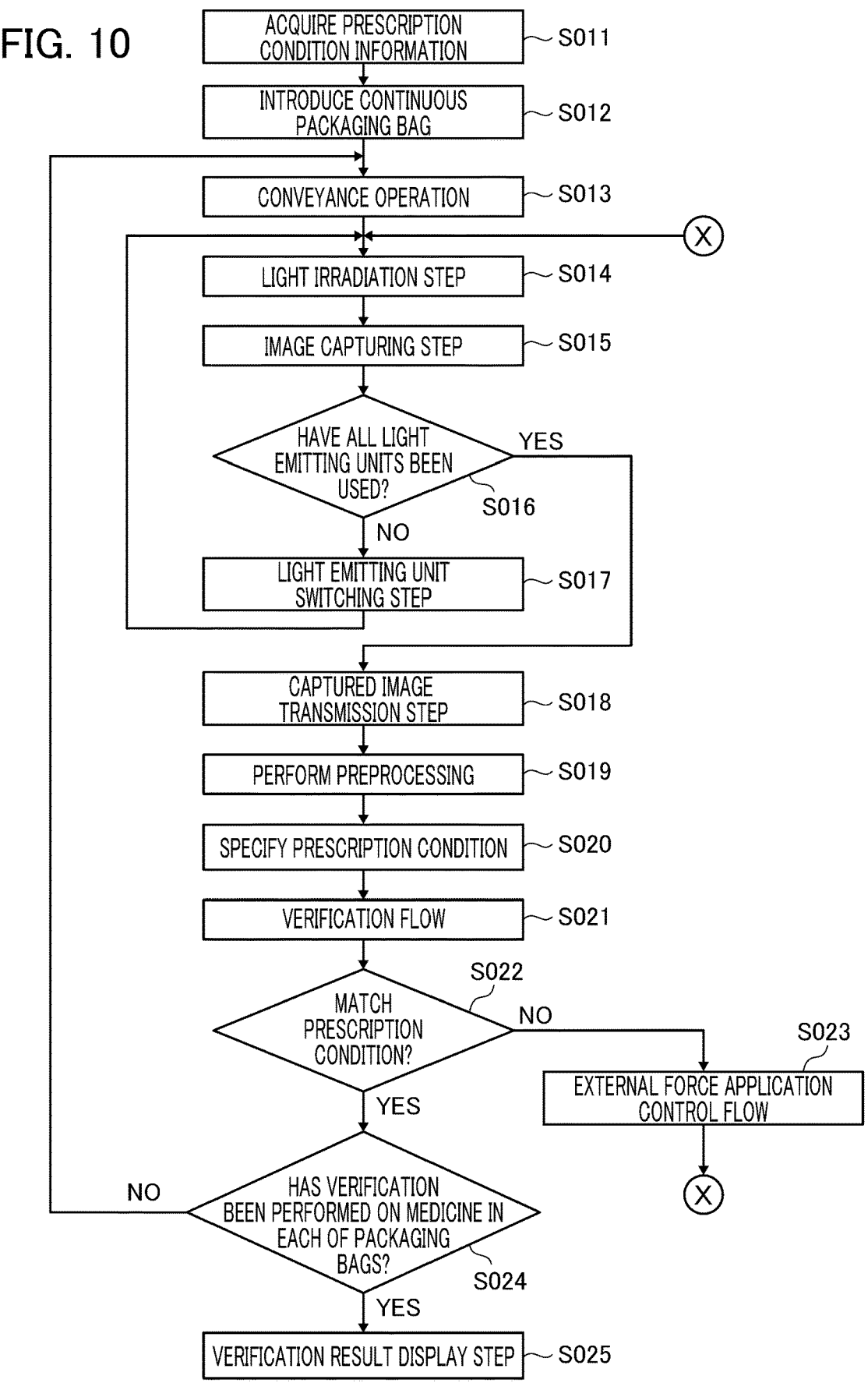
FIG. 10 is a diagram illustrating a flow of operation of a medicine verification device according to one embodiment of the present invention.

Next, operation of the medicine verification device 10 will be described with reference to FIG. 10. FIG. 10 is a diagram illustrating a flow of operation of the medicine verification device 10. The medicine verification method of the present invention is implemented in the operation of the medicine verification device 10 described below. In particular, an external force application control flow and processes related to this flow (specifically, prescription condition information acquisition S011, conveyance operation S013, and image capturing step S015) constitute the medicine verification method of the present invention.

First, after completion of the input of the prescription condition information in the prescription input operation, the prescription condition information acquisition unit 22 of the processing device 12 communicates with the prescription condition input device 50 and acquires the prescription condition information indicating the input prescription condition (S011).

Meanwhile, after the automatic packaging operation is performed by the packaging machine 60 in accordance with the input prescription condition (in other words, the prescription condition indicated by the prescription condition information acquired by the prescription condition information acquisition unit 22), the continuous packaging bag 3 having a strip-like shape including the continuously connected packaging bags 1 each of which contains the medicine is created. The continuous packaging bag 3 is introduced into the device main body 11 by the introduction part 13a formed in the housing 13 of the device main body 11 (S012).

After the continuous packaging bag 3 is introduced into the device main body 11, the conveyance operation by the conveyance unit 14 is intermittently repeated (S013). In each of conveyance operations, the continuous packaging bag 3 is conveyed by a predetermined amount to the downstream side in the conveyance direction. When the continuous packaging bag 3 is conveyed to the downstream side in the conveyance direction, one of the packaging bags 1 among the continuous packaging bag 3 is eventually disposed on the arrangement unit 15. Each time the conveyance operation is performed, the packaging bag 1 disposed on the arrangement unit 15 among the continuous packaging bag 3 is switched.

During a period between one conveyance operation and the next conveyance operation (that is, during stoppage of the conveyance of the continuous packaging bag 3), the light irradiation unit 17 emits light to the medicine packed in the packaging bag 1 disposed on the arrangement unit 15 (S014). In this state, using each of cameras, namely, the first camera 16a and the second camera 16b, the image capturing unit 16 captures an image (that is, a verification target medicine) packed in the packaging bag 1 disposed on the arrangement unit 15 (S015).

The light irradiation step S014 by the light irradiation unit 17 will be described in detail. The light irradiation unit 17 emits light from one of the four light emitting units 17a, 17b, 17c, and 17d disposed around the arrangement unit 15, switches the light emitting units sequentially (S016 and S017), and then, emits light again from the newly switched light emitting unit 17a, 17b, 17c, or 17d. That is, the light irradiation unit 17 sequentially switches the light irradiation directions and emits light from each of directions.

Subsequently, the image capturing unit 16 captures an image of the verification target medicine for each of light irradiation directions. This enables a total of eight images (the number of cameras x the number of light irradiation directions) to be captured for the medicine packed in the packaging bag 1 disposed on the arrangement unit 15.

The light irradiation step S014, the image capturing step S015, and the light emitting unit switching step S017 described above are repeatedly performed every time the packaging bag 1 disposed on the arrangement unit 15 is switched together with the conveyance operation.

The captured image is transmitted to the image acquisition unit 23 of the processing device 12 as needed (S018).

Thereafter, preprocessing is performed by the preprocessing unit 24 of the processing device 12 on the image acquired by the image acquisition unit 23 (S019). This generates a preprocessed image that emphasizes edges of the identification information formed by engraving on the surface of the medicine.

Meanwhile, the verification unit 25 of the processing device 12 specifies a prescription condition for the medicine (that is, the verification target medicine) appearing in the preprocessed image (S020). Specifically, based on the prescription condition information acquired in S011, the verification unit 25 specifies the prescription conditions set for the medicine packaged in each of the packaging bags 1 in the continuous packaging bag 3 (specifically, the type and the number of medicine for each of types).

Thereafter, the verification unit 25 verifies the type of the medicine packaged in each of the packaging bags 1 in the continuous packaging bag 3 following the procedure of the above-described verification flow (S021). In the verification flow, the verification unit 25 accesses the database DB of the database server 70 and reads the master image corresponding to the prescription condition (specifically, the type of medicine) specified in the previous step S020. Subsequently, the verification unit 25 verifies the type and the number of medicines packed in the packaging bag 1 disposed on the arrangement unit 15 using the preprocessed image and the master image.

In a case where the type and number of the medicines packed in one packaging bag 1 match the prescription conditions (Yes in S022), a series of steps S013 to S021 from the conveyance operation to the verification flow described above will be performed again. That is, the packaging bag 1 adjacent to the one packaging bag 1 on the upstream side will now be disposed on the arrangement unit 15, and then, steps including the light irradiation step S014, the image capturing step S015, and the light emitting unit switching step S017 and the verification flow by the verification unit 25 will be performed on the medicine in the packaging bag 1 defined as the verification target medicine.

In contrast, in a case where the type and number of the medicines packed in one packaging bag 1 do not match the prescription conditions (No in S022), an external force application control flow described below is first performed (S023), and then, the process returns to the above-described light irradiation step S014. The subsequent steps S015 to S021 will be repeated in the above-described procedure. In other words, in a case where the type and number of the medicines packed in one packaging bag 1 do not match the prescription conditions, the steps including the light irradiation step S014, the image capturing step S015, the light emitting unit switching step S017, and the verification flow by the verification unit 25 will be repeated in a state where the same packaging bag 1 remains disposed on the arrangement unit 15.

Thereafter, a series of steps S013 to S021 is repeatedly performed for all the packaging bags 1 in the continuous packaging bag 3, every time of switching the packaging bags 1 disposed on the arrangement unit 15, until completion of the verification for the medicine packed in the packaging bags 1 (S024).

The verification unit 25 performs the above-described verification with the medicine packaged in each of the packaging bags 1 in the continuous packaging bag 3 as a verification target. After completion of all verifications, the verification unit 25 displays character information indicating the verification result on a display (not illustrated) (S025). Specifically, the verification unit 25 displays, on the display, character information for notification of the verification result regarding the type of the medicine packed in each of the packaging bags 1 in the continuous packaging bag 3.

The verification result to be displayed on the display may be displayed in any manner as long as it is possible to clearly grasp which packaging bag 1 in the continuous packaging bag 3 is the verification result for the medicine packed in the packaging bag 1. Accordingly, the verification results may be displayed by switching for each of the packaging bags, or verification result for each of the packaging bags 1 in the continuous packaging bag 3 may be displayed collectively in association with the position or order of the packaging bag 1.

Thereafter, the conveyance operation of the conveyance unit 14 allows the continuous packaging bag 3 to reach the discharge part of the housing 13 of the device main body 11, and the packaging bag 1 at the end of the continuous packaging bag 3 (the packaging bag 1 located most upstream in the conveyance direction) is discharged out of the housing 13, and the basic operation of the medicine verification device 10 is completed at this point.

<<External Force Application Unit>>

Next, the external force application unit 40 included in the device main body 11 of the medicine verification device 10 will be described in detail. The external force application unit 40 performs an external force applying operation to apply an external force to each of medicines (that is, verification target medicine) packed in the packaging bag 1 disposed on the arrangement unit 15 to move the medicine within the packaging bag 1 disposed on the arrangement unit 15. The external force applying operation of the external force application unit 40 allows the medicine in the packaging bag 1 disposed on the arrangement unit 15 to move or change its posture within the packaging bag 1. With execution of this operation, it is possible to spread the medicines when they are densely packed in the packaging bag 1 disposed on the arrangement unit 15, lay down the medicines when they stand upright, or move the medicine to approach a predetermined range when its position is out of the range.

The external force application unit 40 according to the present embodiment applies vibration, as an external force, to the medicine (that is, the verification target medicine) packed in the packaging bag 1 disposed on the arrangement unit 15. An example of the applicable external force application unit 40 that applies vibration is the external force application unit 40 illustrated in FIG. 3. The external force application unit 40 illustrated in FIG. 3 includes: a leaf spring 41 supported in a cantilever state; and a drive source (not illustrated) that vibrates the leaf spring 41. The leaf spring 41 is disposed in the vicinity of the arrangement unit 15, with its free end located immediately below the upstream end of the arrangement unit 15 in the conveyance direction. When the drive source is activated to vibrate the free end of the leaf spring 41 (with vertical movement), the vibration of the leaf spring 41 is transmitted to the packaging bag 1 and the medicine inside the packaging bag 1 via the arrangement unit 15. With this configuration, a vibration as an external force is applied to the verification target medicine. As a result, the position of the medicine changes, or the medicine in the upright posture lies down.

The transmission path of the vibration of the leaf spring 41 is not limited to the case where the vibration is transmitted to the packaging bag 1 and the medicine packed in the packaging bag 1 via the arrangement unit 15. For example, the leaf spring 41 may vibrate while being in contact with the packaging bag 1, and the vibration may be directly transmitted to the packaging bag 1 disposed on the arrangement unit 15.

Furthermore, while only one leaf spring 41 is provided in the external force application unit 40 illustrated in FIG. 3, the present invention is not limited to this, and a plurality of leaf springs 41 and a plurality of drive sources for vibrating the leaf spring 41 may be provided. Moreover, the arrangement position of the leaf spring 41 is not limited and may be arranged at a position other than the position illustrated in FIG. 3 (that is, the position directly below the upstream end of the arrangement unit 15 in the conveyance direction).

Figure 11:
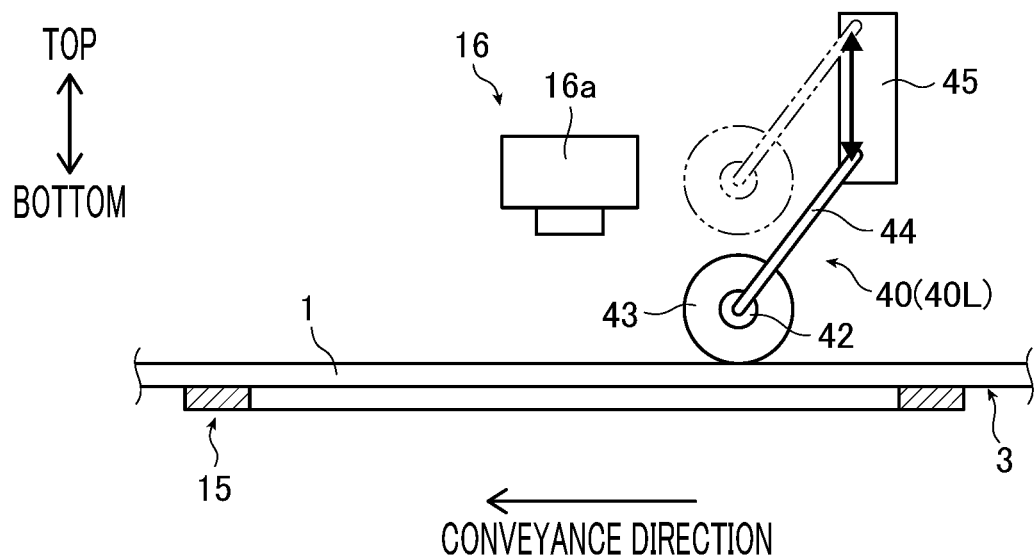
FIG. 11 is a schematic view illustrating a second example of an external force application unit.

Furthermore, the external force application unit 40 is not limited to the one using the leaf spring 41, and other examples are also conceivable. For example, an external force application unit 40 illustrated in FIG. 11 (hereinafter, an external force application unit 40L of a second example) is also applicable. FIG. 11 is a schematic view illustrating the external force application unit 40L of the second example.

As illustrated in FIG. 11, the external force application unit 40L of the second example includes: a support shaft 42 arranged along the intersecting direction; a roller 43 rotatably supported by the support shaft 42; an arm 44 that grips the support shaft 42; an elevating/lowering mechanism 45 for elevating and lowering the arm 44; and a driving mechanism (not illustrated) that moves the elevating/lowering mechanism 45 to elevate and lower the arm 44.

The roller 43 has an outer peripheral portion formed of an elastic body such as rubber or sponge and rotates integrally with the support shaft 42. In the external force application unit 40L of the second example illustrated in FIG. 11, the roller 43 is arranged at a position above the arrangement unit 15. Furthermore, an overall length (length in the axial direction) of the roller 43 is longer than a lateral width of the continuous packaging bag 3 (that is, the lateral width of the packaging bag 1). The arm 44, elevated and lowered by the function of the elevating/lowering mechanism 45, is normally set at an upper end position (the position illustrated in broken line in FIG. 11), while it is set at a lower end position (position illustrated in solid line in FIG. 11) when the external force application unit 40L of the second example is used. When the arm 44 is at the upper end position, the roller 43 is located above the arrangement unit 15 and is separated from the continuous packaging bag 3. In contrast, when the arm 44 is at the lower end position, as illustrated in FIG. 11, the outer peripheral portion of the roller 43 comes into contact with the continuous packaging bag 3, particularly with the packaging bag 1 disposed on the arrangement unit 15. At this time, the outer peripheral portion of the roller 43 comes in contact with the packaging bag 1 over a portion from one end to the other end of the packaging bag 1 in the intersecting direction.

Subsequently, when the roller 43 comes into contact with the packaging bag 1 disposed on the arrangement unit 15, the conveyance unit 14 conveys the continuous packaging bag 3 so that the entire surface of the packaging bag 1 disposed on the arrangement unit 15 (the entire upper surface facing the roller 43) comes into contact with the roller 43. At this time, the outer peripheral portion of the roller 43 presses the medicine packed in the packaging bag 1 (that is, the verification target medicine) via the packaging bag 1 disposed on the arrangement unit 15. As a result, a pressing force as an external force is applied to the verification target medicine, thereby leveling the medicine within the packaging bag 1. Thereafter, the conveyance unit 14 conveys the continuous packaging bag 3 by the same amount as the conveyed amount in a direction opposite to the direction of the immediately preceding conveyance.

In the external force application unit 40L of the above-described second example, the conveyance unit 14 conveys the continuous packaging bag 3 in the state where the packaging bag 1 is in contact with the roller 43 in application of an external force (pressing force) to the medicine packed in the packaging bag 1 disposed on the arrangement unit 15. However, the present invention is not limited to this. For example, the roller 43 itself may move downstream in the conveyance direction in the state where the roller 43 is in contact with the packaging bag 1 disposed on the arrangement unit 15.

Figure 12:
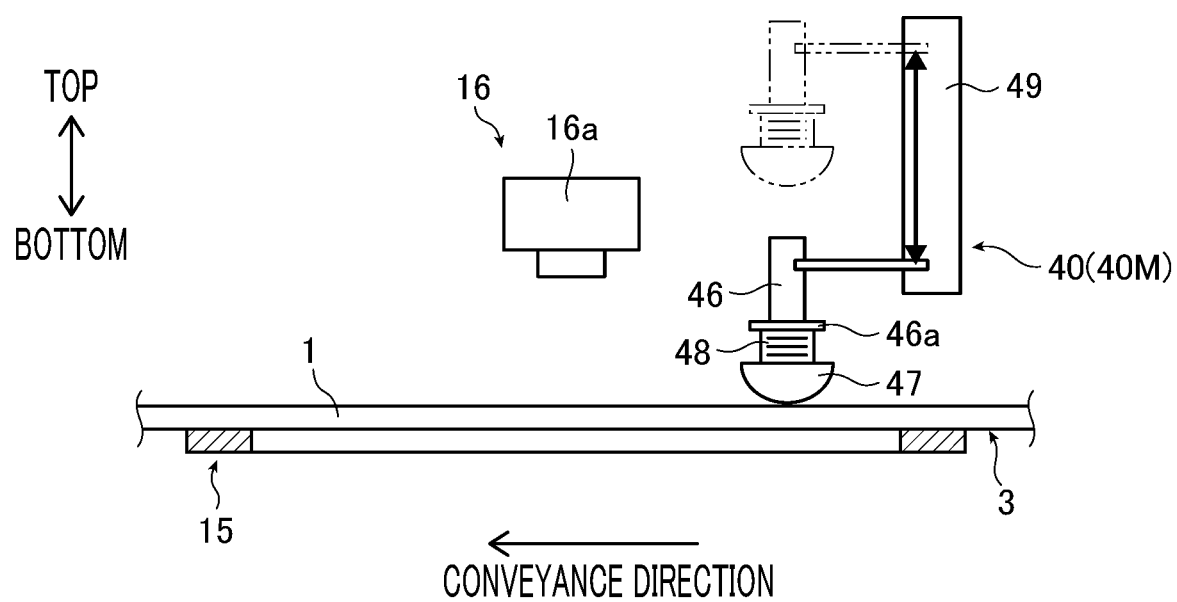
FIG. 12 is a schematic view illustrating a third example of an external force application unit.

Furthermore, an external force application unit 40 illustrated in FIG. 12 (hereinafter, an external force application unit 40M of a third example) is also applicable. FIG. 12 is a schematic view illustrating the external force application unit 40M of the third example.

The external force application unit 40M of the third example includes: a shaft 46 arranged along the vertical direction; a contact portion 47 attached to the tip of the shaft 46; a coil spring 48 attached to the shaft 46 so as to be extendable and contractible; a retainer 46a having a flange shape and provided at an end opposite to the tip of the shaft 46; an elevating/lowering mechanism 49 for elevating/lowering the shaft 46; and a driving mechanism (not illustrated) for moving the elevating and lowering mechanism 49 to elevate and lower the shaft 46. Note that a combination of the shaft 46, the contact portion 47, the coil spring 48, the retainer 46a, and the elevating/lowering mechanism 49 is provided in plurality with a regular pitch in the intersecting direction.

The contact portion 47 is formed of a soft material such as rubber or sponge. The contact portion 47 has a lower surface (contact surface) being a hemispherical surface or a curved surface and is biased downward by the coil spring 48.

In the external force application unit 40M of the third example illustrated in FIG. 12, the shaft 46 and the contact portion 47 are arranged above the arrangement unit 15. The shaft 46, elevated and lowered by the function of the elevating/lowering mechanism 49, is normally set at an upper end position (the position illustrated in broken line in FIG. 12), while it is set at a lower end position (position illustrated in solid line in FIG. 12) when the external force application unit 40M of the third example is used. When the shaft 46 is at the upper end position, the contact portion 47 is located above the arrangement unit 15 and is separated from the continuous packaging bag 3. In contrast, when the shaft 46 is at the lower end position, as illustrated in FIG. 12, the lower surface of the contact portion 47 comes into contact with the continuous packaging bag 3, particularly with the packaging bag 1 disposed on the arrangement unit 15.

When the lower surface of the contact portion 47 comes into contact with the packaging bag 1 disposed on the arrangement unit 15, the elevating/lowering mechanism 49 once raises the shaft 46 to a position where the contact portion 47 is slightly spaced from the packaging bag 1, and thereafter lowers the shaft 46 again to bring the lower surface of the contact portion 47 into contact with the packaging bag 1 again. While repeating such vertical movement of the contact portion 47, the conveyance unit 14 conveys the continuous packaging bag 3 so that the entire surface of the packaging bag 1 (the entire upper surface facing the contact portion 47) disposed on the arrangement unit 15 is brought into contact with the contact portion 47. At this time, the lower surface of the contact portion 47 hits against the medicine packed in the packaging bag 1 (that is, the verification target medicine) via the packaging bag 1 disposed on the arrangement unit 15. As a result, an impact as an external force is applied to the verification target medicine, thereby laying down the medicine standing upright within the packaging bag 1. Thereafter, the conveyance unit 14 conveys the continuous packaging bag 3 by the same amount as the conveyed amount in a direction opposite to the direction of the immediately preceding conveyance.

In the external force application unit 40M of the above-described third example, the conveyance unit 14 conveys the continuous packaging bag 3 in the state where the shaft 46 and the contact portion 47 reciprocate in vertical directions in application of an external force (impact) to the medicine packed in the packaging bag 1 disposed on the arrangement unit 15. However, the present invention is not limited to this. For example, the shaft 46 and the contact portion 47 may further move in the conveyance direction while reciprocating vertically.

The external force application unit 40 can be implemented as a fourth example as a further modification. The external force application unit 40 of the fourth example is implemented by the conveyance unit 14 described above. More specifically, as an external force applying operation, the conveyance unit 14 alternates an operation of conveying the continuous packaging bag 3 by a predetermined amount downstream in the conveyance direction and an operation of returning the continuous packaging bag 3 by a predetermined amount upstream in the conveyance direction. The conveyance amount in each of the conveyance operations at this time is set to a very small conveyance amount. The packaging bag 1 disposed on the arrangement unit 15 swings in the conveyance direction by such alternate conveyance operations on the upstream side and the downstream side in the conveyance direction. As a result, a swing as an external force is applied to the medicine (verification target medicine) packed in the packaging bag 1 disposed on the arrangement unit 15, thereby leveling the medicine within the packaging bag 1.

The external force application unit 40 has been described above with reference to some configuration examples. That is, the present embodiment has described an external force application unit 40 that applies any one of vibration, swing, impact, or pressing force as an external force to the medicine packed in the packaging bag 1 disposed on the arrangement unit 15. However, the external force application unit 40 is not limited to the above configuration example. In addition to the above configuration examples, it is also possible to use with no restriction, as the external force application unit 40, a member that can move the medicine in the packaging bag 1, such as hitting, stroking, shaking, and rubbing the packaging bag 1 disposed on the arrangement unit 15. Furthermore, the external force application unit 40 can be implemented by using any one of the above-described configuration examples, or by combining some of the above-described configuration examples.

<<Conditions for Operating External Force Application Unit>>

Next, a condition for the external force application unit 40 to execute the external force applying operation, that is, an operation execution condition will be described.

The external force application unit 40 is controlled by the control unit 21 included in the processing device 12 of the medicine verification device 10. When the operation execution condition is satisfied, the control unit 21 causes the external force application unit 40 to execute the external force applying operation.

More specifically, as illustrated in FIG. 6, the processing device 12 of the medicine verification device 10 includes a condition determination unit 26 that determines whether an operation execution condition is satisfied. When the condition determination unit 26 determines that the operation execution condition of the external force applying operation is satisfied, the control unit 21 causes the external force application unit 40 to execute an external force applying operation of applying an external force to the verification target medicine in the packaging bag 1 disposed on the arrangement unit 15 at a point of acquisition of the determination result by the condition determination unit 26.

The condition determination unit 26 will be described. When the verification unit 25 has verified that the types and the numbers of the medicines (that is, the verification target medicines) packed in the packaging bag 1 disposed on the arrangement unit 15 do not match, the condition determination unit 26 determines whether the operation execution condition is satisfied. The determination as to whether the operation execution condition is satisfied is performed on the medicine in the packaging bag 1 (that is, the verification target medicine) disposed on the arrangement unit 15 at the point of the determination.

Using the images obtained for the packaging bag 1 disposed on the arrangement unit 15 and for the medicine packed in the packaging bag 1 at the point of determining whether the operation execution condition is satisfied, the condition determination unit 26 determines whether the operation execution condition is satisfied. Here, the images used by the condition determination unit 26 are the image acquired by the image acquisition unit 23 and the preprocessed image obtained by the preprocessing executed by the preprocessing unit 24.

Here, the operation execution condition will be described. In the present embodiment, the operation execution condition includes first to fifth operation execution conditions as described below. The following will describe the details of each of operation execution conditions and a method of determining whether each of the operation execution conditions is satisfied.

(First Operation Execution Condition)

The first operation execution condition is a condition that the number of medicines in the captured image of the packaging bag 1 disposed on the arrangement unit 15 at the point of the condition satisfaction determination, that is, the number of verification target medicines is different from the quantity of medicines specified from the prescription condition information (specifically, the quantity to be packaged in the packaging bag 1), and more specifically, a condition that the number is smaller than the quantity of the medicines specified from the prescription condition information. For example, when the medicines overlap in the packaging bag 1 and one medicine is covered and hidden by another medicine, the first operation execution condition can be satisfied.

The condition determination unit 26 determines whether the first operation execution condition is satisfied by using the image of the packaging bag 1 disposed on the arrangement unit 15, more precisely, the preprocessed image. More specifically, the condition determination unit 26 counts the number of medicine images (that is, medicine extraction images X) extracted from the preprocessed image in the medicine presence region specifying step S001 and the pixel group extracting step S002 of the verification flow. The condition determination unit 26 compares the number of extracted medicine extraction images X with the quantity of medicines specified from the prescription condition information. When the number of the medicine extraction images X is smaller than the quantity of medicines specified from the prescription condition information, the condition determination unit 26 determines that the first operation execution condition is satisfied. In determining whether the first operation execution condition is satisfied, the condition determination unit 26 can use the result of the verification by the verification unit 25, more specifically, the unit can use the number of medicines for individual types counted in the verification flow by the verification unit 25.

(Second Operation Execution Condition)

The second operation execution condition is a condition that the shape of the medicine in the captured image of the packaging bag 1 disposed on the arrangement unit 15 at the point of the condition satisfaction determination, that is, the shape of the verification target medicine is different from the shape corresponding to the type of medicine specified from the prescription condition information.

More specifically, the second operation execution condition is a condition that the shape of the verification target medicine appearing in the image captured by the image capturing unit 16 is different from the shape of the medicine captured in the master image corresponding to the type of medicine specified from the prescription condition information. Here, the shape of the medicine appearing in the master image is the shape of a rectangle when the medicine is cut out from the master image (that is, a rectangle surrounding the medicine). The shape of a circular medicine is a square in a normal state and becomes a rectangle when the medicine stands upright. For example, the second operation execution condition can be satisfied when a circular medicine is disposed upright in the packaging bag 1 and thus the medicine takes a shape different from the shape in the normal state, that is, when the medicine takes a rectangular shape because the medicine stands upright. For determination as to whether the shape of the medicine is a square or a rectangle, a known shape verification technique can be used. For example, the verification can be made by measuring individual sides of the rectangle that is the shape of the medicine.

The condition determination unit 26 determines whether the second operation execution condition is satisfied by using the image of the packaging bag 1 disposed on the arrangement unit 15, more precisely, the preprocessed image. More specifically, using a medicine image (that is, a medicine extraction image X) extracted from the preprocessed image in the medicine presence region specifying step S001 and the pixel group extracting step S002 of the verification flow, and using a master image read in the master image reading step S003, the condition determination unit 26 determines whether the outer shapes of the medicines appearing in individual images are different from each other. At this time, the condition determination unit 26 can use the result of verification by the verification unit 25, and more specifically, the unit can use the similarity (correlation value) evaluated by the template matching by the verification unit 25.

Subsequently in a case where the outer shape of the medicine appearing in the medicine extraction image X is different from the outer shape of the medicine appearing in the master image, the condition determination unit 26 determines that the second operation execution condition is satisfied.

(Third Operation Execution Condition)

The third operation execution condition is a condition that a plurality of medicines are disposed on the arrangement unit 15 as verification target medicines and that one and another of the plurality of medicines are adjacent to each other in the irradiation direction in which the light irradiation unit 17 performs light emission.

More specifically, the third operation execution condition is a condition that a plurality of medicines are disposed on the arrangement unit 15 (in other words, a plurality of medicines are present in the packaging bag 1 disposed on the arrangement unit 15) and that one medicine and another medicine having greater thickness than the one medicine are adjacent to each other in the irradiation direction in a state where the another medicine is disposed at a position that blocks light emitted from the light irradiation unit 17.

Figure 13:
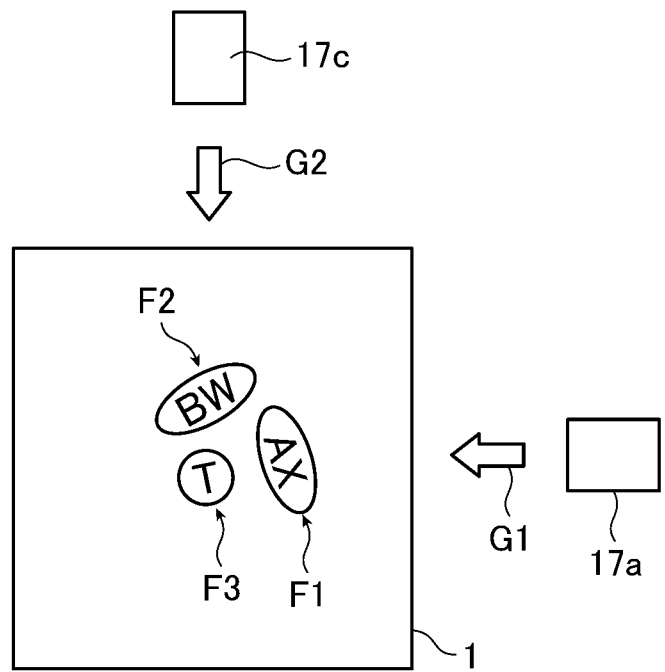
FIG. 13 is a view illustrating a third operation execution condition (part 1).
Figure 14:
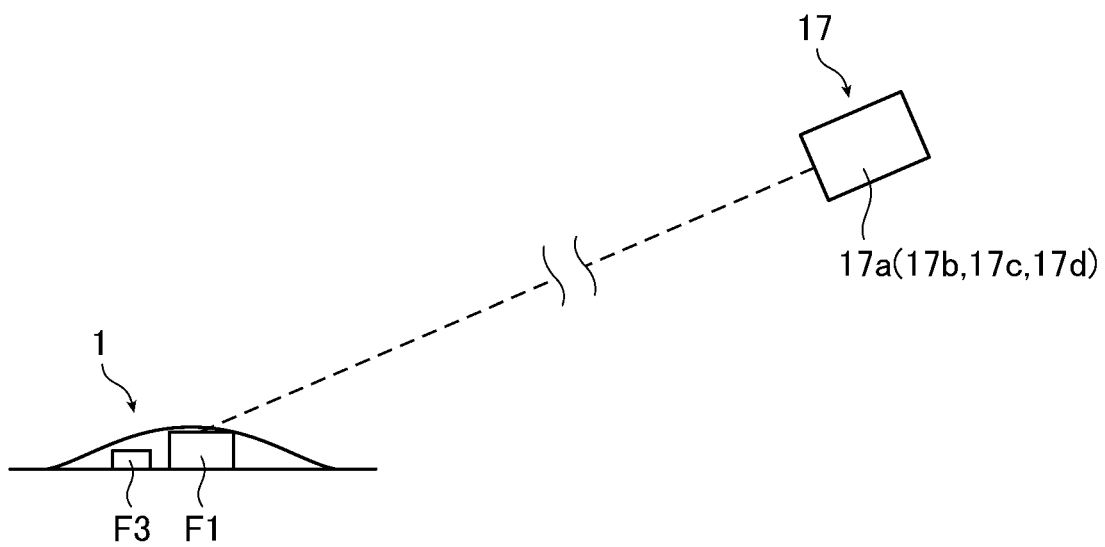
FIG. 14 is a view illustrating a third operation execution condition (part 2).

Hereinafter, the third operation execution condition will be described in an easily understandable way with reference to FIGS. 13 and 14. FIGS. 13 and 14 are views illustrating the third operation execution condition. Specifically, FIG. 13 is a top view of the medicines packaged in the packaging bag 1, and FIG. 14 is a schematic cross section of the medicines packaged in the packaging bag 1.

The following is a case where three types of medicines F1, F2, and F3 are packaged in the packaging bag 1, as a specific example. In addition, it is assumed that each of the three types of medicines F1, F2, and F3 has a plan view size of S1, S2, and S3, and a thickness of d1, d2, and d3, respectively, and these values satisfy the following relational expressions (1) and (2).

$$S3<S2<S1 \qquad (1)$$

$$d3<d2<d1 \qquad (2)$$

In the case illustrated in FIG. 13, the medicine F3 (corresponding to one medicine) is adjacent to the medicine F1 (corresponding to another medicine) in the light irradiation direction (the direction indicated by a symbol G1 in FIG. 13). Here, the thickness of the medicine F1 is greater than the thickness of the medicine F3. The medicine F1 is located at a position closer to the light irradiation source (that is, the light emitting unit 17*a*) in a light irradiation direction G1. Therefore, as illustrated in FIG. 14, the medicine F1 exists at a position that blocks light emitted from the light irradiation unit 17, viewed from the medicine F3. The third operating condition is satisfied in such a situation.

As illustrated in FIG. 14, the light blocking position is a position that is closer to a light irradiation source than an adjacent medicine (a medicine at which light is blocked) and that is a position in the middle of the path of the light emitted from the light irradiation unit 17 (indicated by a broken line in FIG. 14).

Incidentally, in the case illustrated in FIG. 13, the medicine F2 is adjacent to the medicine F3 in the light irradiation direction (the direction indicated by the symbol G2 in FIG. 13), the thickness of the medicine F2 is greater than the thickness of the medicine F3, and the medicine F2 is located at a position close to the light irradiation source (that is, the light emitting unit 17*c*) in the light irradiation direction G2. Therefore, the medicine F2 exists at a position that blocks light emitted from the light irradiation unit 17, viewed from the medicine F3. That is, in the case illustrated in FIG. 13, a plurality of combinations of medicines adjacent to each other in the light irradiation direction exist.

The condition determination unit 26 determines whether the third operation execution condition is satisfied using an image of the packaging bag 1 disposed on the arrangement unit 15, more precisely, an image captured by the image capturing unit 16 in each of light irradiation directions. More specifically, the condition determination unit 26 specifies the positional relationship between the medicines in each of the captured images in each of the light irradiation directions, and then verifies whether the medicine having a greater thickness is adjacent to the medicine having a smaller thickness at a position close to the light emitting unit 17*a*, 17*b*, 17*c*, or 17*d*, (more precisely, the light emitting unit emitting light at the time of image capturing) in the light irradiation direction.

More specifically, the condition determination unit 26 specifies the direction of light emission (in other words, which of the four light emitting units 17*a*, 17*b*, 17*c*, and 17*d* has been used) during image capturing, and confirms whether a plurality of medicines adjacent to each other in the specified light irradiation direction exist in the captured image. In a case where a plurality of medicines adjacent to each other in the light irradiation direction exist as a result of the confirmation, the magnitude relationship between the thicknesses of these medicines is specified.

A procedure of specifying the magnitude relationship between the thicknesses of the medicines will be described. The condition determination unit 26 analyzes the captured image and specifies the plan view size of each of the plurality of medicines adjacent to each other. In addition, the condition determination unit 26 specifies the thickness of each of the plurality of medicines adjacent to each other on the basis of the specified plan view size of each of medicines and the prescription condition information acquired by the prescription condition information acquisition unit 22. More specifically, the condition determination unit 26 reads the database DB from the database server 70, and specifies, from the database DB, a plan view size and the thickness of the medicine corresponding to the type of medicine indicated by the prescription condition information acquired by the prescription condition information acquisition unit 22. The condition determination unit 26 calculates a thickness corresponding to the specified plan view size for each of the plurality of medicines adjacent to each other. For example, when the database DB illustrated in FIG. 9 is used, the thickness of the medicine having the plan view size S1 is the thickness (that is, h1) of the medicine assumed to be type F1.

With the above procedure, the condition determination unit 26 specifies the thickness of each of the plurality of medicines adjacent to each other and then determines whether the medicine having a greater thickness is adjacent to the medicine having a smaller thickness at a position close to the light emitting unit 17a, 17b, 17c, or 17d (more precisely, the light emitting unit emitting light at the time of image capturing) in the light irradiation direction. In a case where it is determined that the medicine having a greater thickness is located, adjacent to the medicine having a smaller thickness, at a position close to the light emitting unit 17a, 17b, 17c, or 17d in the light irradiation direction, the condition determination unit 26 determines that the third operation execution condition is satisfied.

In the present embodiment, as described above, it is determined that the third operation execution condition is satisfied in a case where a medicine having a greater thickness is located, adjacent to a medicine having a smaller thickness, at a position close to the light emitting unit 17a, 17b, 17c, or 17d in the light irradiation direction. However, the present invention is not limited to this, and it is allowable to determine that the third operation execution condition is satisfied in a case where a plurality of medicines are adjacent to each other in the light irradiation direction regardless of the magnitude of the thickness.

(Fourth Operation Execution Condition)

The fourth operation execution condition is a condition that the arrangement position of the verification target medicine appearing in the captured image in the arrangement unit 15 is a position within a predetermined region. Here, the predetermined region is a region where the distance from the light emitting unit 17a, 17b, 17c, or 17d of the light irradiation unit 17 in the light irradiation direction is a threshold or more.

Figure 15:
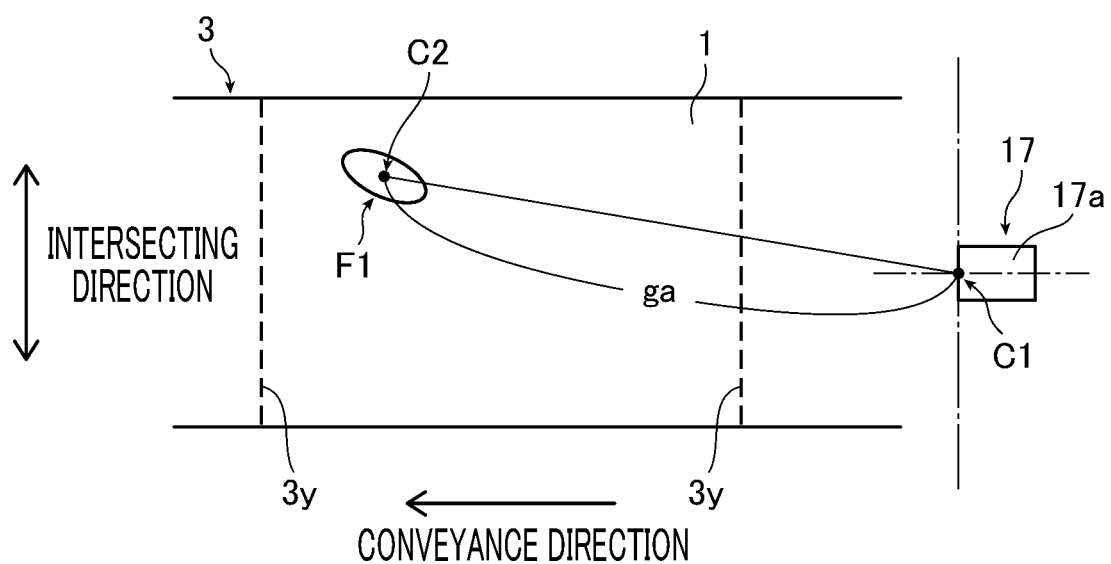
FIG. 15 is a view illustrating a fourth operation execution condition.

More specifically, the fourth operation execution condition is a condition that the arrangement position of the verification target medicine appearing in the image captured by the image capturing unit 16 is separated from one of the light emitting units 17a, 17b, 17c, and 17d that was emitting light at that time, by a threshold or more. For example, as illustrated in FIG. 15, the fourth operation execution condition is satisfied in a case where one of the medicines (the medicine F1 in FIG. 15) in the packaging bag 1 disposed on the arrangement unit 15 is separated from the light emitting unit 17a that emits light at the point of image capturing, by a threshold or more. FIG. 15 is a view illustrating the fourth operation execution condition. For the sake of convenience, FIG. 15 illustrates only one medicine packed in the packaging bag 1.

The condition determination unit 26 determines whether the fourth operation execution condition, which uses an image of the packaging bag 1 disposed on the arrangement unit 15, more precisely, an image captured by the image capturing unit 16 in each of light irradiation directions, is satisfied.

Specifically, the condition determination unit 26 uses the procedure similar to the medicine presence region specifying step S001 and the pixel group extracting step S002 of the verification flow and thereby extracts a medicine image (pixel group including an image of the medicine) from the captured image for each of irradiation directions. Furthermore, the condition determination unit 26 specifies the arrangement position (more precisely, a center coordinate position of the medicine with respect to a reference position) of the medicine appearing in the extracted medicine image, in the arrangement unit 15. Furthermore, the condition determination unit 26 specifies the center coordinate position of the light emitting surface (surface facing the arrangement unit 15) of the light emitting unit 17a, 17b, 17c, or 17d emitting light at that point. Simply put, in the case illustrated in FIG. 15, the position of the coordinate C1 is specified as the center position of the light emitting surface of the light emitting unit 17a, and the position of the coordinate C2 is specified as the arrangement position of the medicine F1.

Thereafter, the condition determination unit 26 calculates a distance between the two specified coordinate positions (the distance denoted by a symbol ga in FIG. 15) and then determines whether the calculated distance ga is a threshold or more. Here, the threshold is a value stored in advance in the memory of the processing device 12. Specifically, the distance ga at a time when the illuminance at light emission from the light emitting unit 17a, 17b, 17c, or 17d falls below a control value is stored as the threshold.

The condition determination unit 26 reads the threshold from the memory when determining whether the fourth operation execution condition is satisfied and then determines that the fourth operation execution condition is satisfied in a case where the calculated distance ga is the threshold or more.

The threshold may be the same (common) value among the four light emitting units 17a, 17b, 17c, and 17d, or may be different for each of the light emitting units 17a, 17b, 17c, and 17d.

(Fifth Operation Execution Condition)

The fifth operation execution condition is a condition that the posture of the medicine (that is, the verification target medicine) appearing in the image captured by the image capturing unit 16 is a posture that causes the identification information formed on the surface of the medicine to be outside an imaging range of the image capturing unit 16 (more precisely, the imaging range of each of the first camera 16a and the second camera 16b).

More particularly, the fifth operation execution condition is a condition that the posture of the verification target medicine appearing in the image is a posture that causes the identification information formed on the surface of the medicine to go outside the imaging range of each of the first camera 16a and the second camera 16b. For example, in a case where identification information is formed on the surface (outer peripheral surface) of a cylindrical medicine, and the portion where the identification information is formed in the outer peripheral surface of the medicine faces sideways so as to be outside the imaging range of each of the first camera 16a and the second camera 16b, the fifth operation execution condition can be satisfied.

The condition determination unit 26 determines whether the fifth operation execution condition is satisfied by using the image of the packaging bag 1 disposed on the arrangement unit 15, more precisely, the preprocessed image. Specifically, the condition determination unit 26 uses a medicine image (that is, a medicine extraction image X) extracted from the preprocessed image in the medicine presence region specifying step S001 and the pixel group extracting step S002 of the above-described verification flow, and uses a master image read in the master image reading step S003. The condition determination unit 26 compares the medicine appearing in the medicine extraction image X with the medicine appearing in the master image and then determines whether the identification information of the medicine captured in the read master image is also found in the medicine extraction image X. In a case where no portion of the medicine identification information captured in the read master image is found in the medicine extraction image X, the condition determination unit 26 determines that the fifth operation execution condition is satisfied.

While the first to fifth operation execution conditions have been described as operation execution conditions in the present embodiment, it is satisfactory as long as at least one of the first operation execution condition and the second operation execution condition is included in the operation execution condition. It is also allowable that there is a condition not to be adopted, among the above five conditions, and it is allowable to add a condition other than the above five conditions.

<<External Force Application Control Flow>>

Figure 16:
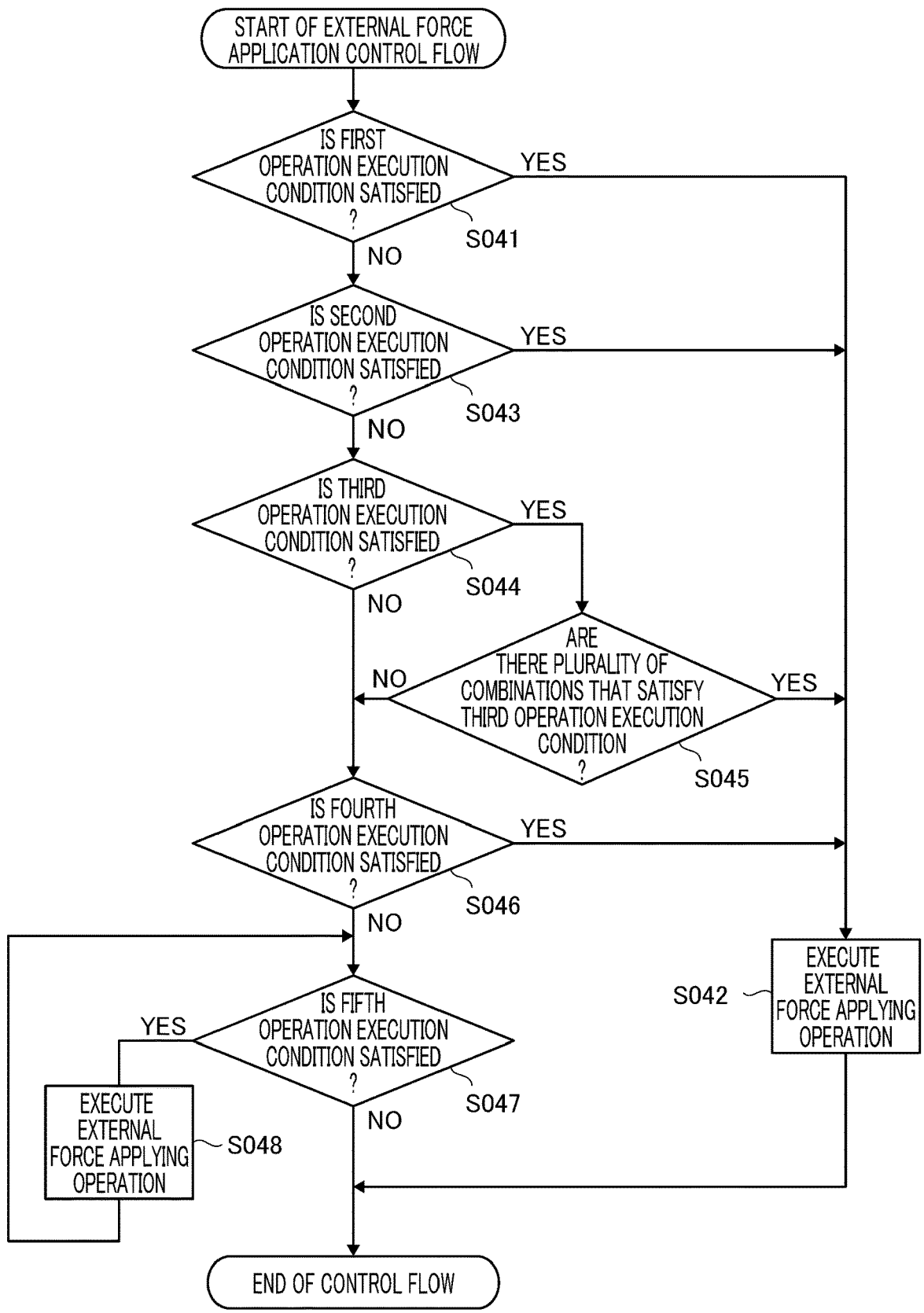
FIG. 16 is a diagram illustrating an external force application control flow.

Next, a flow (hereinafter, a control flow) in which the control unit 21 controls the external force application unit 40 on the basis of whether the above-described operation execution condition is satisfied will be described with reference to FIG. 16. FIG. 16 is a diagram illustrating an external force application control flow.

In the present embodiment, when any one of the above-described five operation execution conditions is satisfied, the control unit 21 causes the external force application unit 40 to execute an external force applying operation. More specifically, while the conveyance operation of the conveyance unit 14 is stopped and one packaging bag 1 among the continuous packaging bag 3 is disposed on the arrangement unit 15, the condition determination unit 26 determines whether each of the operation execution conditions is satisfied by using the above-described procedure (S041, S043, S044, S046, and S047).

In a case where the condition determination unit 26 determines that the first operation execution condition is satisfied (Yes in S041), the control unit 21 causes the external force application unit 40 to execute the external force applying operation for a predetermined time (S042). Thereafter, the control flow ends.

In contrast, in a case where the condition determination unit 26 determines that the first operation execution condition is not satisfied (No in S041), determination is made next as to whether the second operation execution condition is satisfied (S043). In a case where the condition determination unit 26 determines that the second operation execution condition is satisfied (No in S043), the control unit 21 causes the external force application unit 40 to execute the external force applying operation for a predetermined time (S042). Thereafter, the control flow ends.

In contrast, in a case where the second operation execution condition is not satisfied, it is next determined whether the third operation execution condition is satisfied (S044). When it is determined that the third operation execution condition is satisfied (Yes in S044), the condition determination unit 26 further determines whether there are a plurality of combinations in which one medicine and another medicine are adjacent to each other in the light irradiation direction at each of the times of image capturing (S045). In a case where the condition determination unit 26 determines that there are a plurality of the above combinations (Yes in S045), the control unit 21 causes the external force application unit 40 to execute the external force applying operation for a predetermined time (S042). Thereafter, the control flow ends.

By contrast, in a case where the condition determination unit 26 determines that only one of the above combinations exists (No in S045), the control unit 21 would not cause the external force application unit 40 to perform the external force applying operation. Instead, an image captured by light emission in the same direction as a direction in which a plurality of medicines are adjacent to each other, out of the images captured by the image capturing unit 16 for each of the light irradiation directions, will not be adopted, and the remaining images will be used to perform medicine type determination or the like. However, the present invention is not limited to this, and the external force applying operation may be performed even when only one of the above combinations exists.

In a case where the third operation execution condition is not satisfied, or where the third operation execution condition is satisfied but there are no plurality of combinations of medicines adjacent to each other in the light irradiation direction, a determination is next made as to whether the fourth operation execution condition is satisfied (S046). In a case where the condition determination unit 26 determines that the fourth operation execution condition is satisfied (Yes in S046), the control unit 21 causes the external force application unit 40 to execute the external force applying operation for a predetermined time (S042). Thereafter, the control flow ends.

In a case where the fourth operation execution condition is not satisfied, determination will be made as to whether the fifth operation execution condition is satisfied (S047). In a case where the condition determination unit 26 determines that the fifth operation execution condition is satisfied (Yes in S047), the control unit 21 causes the external force application unit 40 to execute the external force applying operation for a predetermined time (S048). After the execution of the external force applying operation, the process returns to step S047, and the condition determination unit 26 determines again whether the fifth operation execution condition is satisfied (S047).

Subsequently, in a case where it is determined in the re-determination that the fifth operation execution condition is still satisfied, the control unit 21 causes the external force application unit 40 to execute the external force applying operation again (S048). In this manner, in the present embodiment, when the fifth operation execution condition is satisfied after the external force application unit 40 executes the external force applying operation, the control unit 21 causes the external force application unit 40 to repeatedly execute the external force applying operation. With this operation, it is possible to repeatedly apply the external force to the medicine until the posture of the medicine in the packaging bag 1 disposed on the arrangement unit 15 becomes a posture that enables the identification information formed on the surface of the medicine to be within the imaging range of the image capturing unit 16.

Subsequently, when the fifth operation execution condition is cancelled (not satisfied), the control flow ends at that point.

After the control flow is completed, as illustrated in FIG. 10, the light irradiation step S014, the image capturing step S015, the light emitting unit switching step S017, and the verification flow performed by the verification unit 25 are repeated for the packaging bag 1 disposed on the arrangement unit 15 at that point and for the medicine packed inside the bag. That is, in the present embodiment, when it is verified that the type and the number of the verification target medicines do not match the prescription conditions, whether the operation execution condition is satisfied is determined, and in a case where the operation execution condition is satisfied, an external force applying operation will be executed; and thereafter, verification is performed again.

It is allowable to set a limit (upper limit) for the number of times of verifications. In a case where a limit (upper limit) is set, the verification target medicine is to be switched to a new medicine (that is, the packaging bag 1 to be disposed on the arrangement unit 15 is switched) when the number of verifications reaches the upper limit, and then, the following verification is to be performed.

<<Effectiveness of the Medicine Verification Device According to the Present Embodiment>>

As described above, the medicine verification device 10 according to the present embodiment determines whether the first to fifth operation execution conditions described above are satisfied at verification of the type of the verification target medicine (specifically, the medicine in the packaging bag 1 disposed on the arrangement unit 15). Subsequently, in a case where any of the operation execution conditions is satisfied, an external force is applied to the verification target medicine so as to level or move the medicine or change the posture of the medicine.

As described above, the medicine verification device 10 of the present embodiment decides whether to apply the external force based on the specific situation of the verification target medicine. Here, the specific situation includes the number and type of the verification target medicines, the irradiation direction of light when capturing an image of the verification target medicine, the presence of an object (another medicine) that blocks the emitted light, the distance from the light emitting unit 17a, 17b, 17c, or 17d configured to emit light, and the posture of the medicine at the time of image capturing (for simplicity, the facing direction of the portion where the identification information is formed on the surface of the medicine), or the like.

In the above points, unlike the medicine verification device described in Patent Literature 1 that determines whether to apply the external force based only on the distribution state of the medicine, the medicine verification device 10 according to the present embodiment is capable of determining whether to apply the external force more properly than the medicine verification device described in Patent Literature 1. In other words, the medicine verification device 10 according to the present embodiment is capable of applying an external force to the verification target medicine when necessary based on the specific situation (specifically, based on the determination result of whether each of the operation execution conditions is satisfied). Accordingly, the medicine verification device 10 of the present embodiment makes it possible to improve the verification accuracy and verification speed as compared with the medicine verification device described in Patent Literature 1.

<<Other Embodiments>>

While the medicine verification device and the medicine verification method of the present invention have been described above with reference to a specific example, the above embodiments are merely an example, and other embodiments are conceivable. For example, while the above-described embodiment is a case where the type or the like of the medicine packed in the packaging bag 1 is verified, the present invention is not limited to this. The verification target medicine in the state not being packed in the packaging bag 1, for example, the medicine in an unpackaged state may be disposed on the arrangement unit 15 to be provided for the verification. Such a case (hereinafter, a modification) corresponds to a case where, for example, a patient brings a medicine, and the medicine is provided for verification (or examination) as to whether the medicine has the content and quantity as instructed in the prescription.

Figure 17:
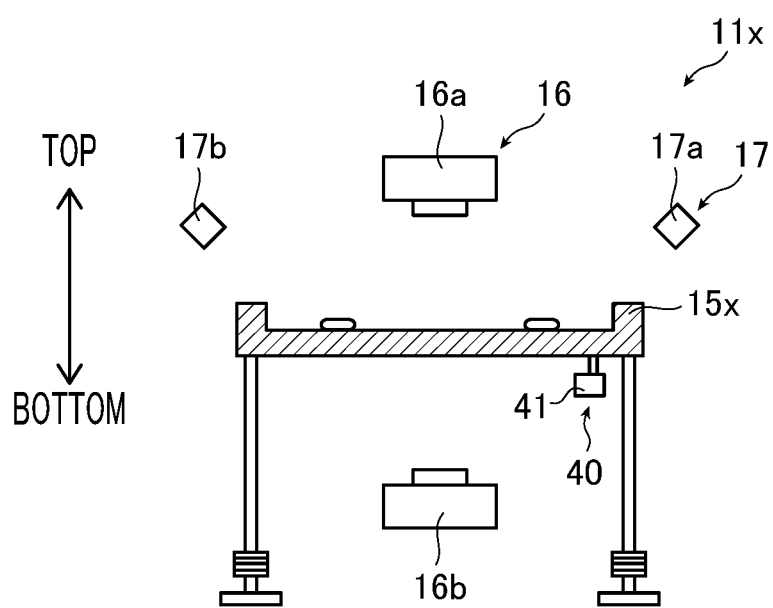
FIG. 17 is a schematic view illustrating a device main body of a medicine verification device according to a modification.

A device main body of a medicine verification device according to a modification will be described. As illustrated in FIG. 17, a device main body 11x of the medicine verification device according to the modification includes an arrangement unit 15x that arranges the medicine that is not packed in the packaging bag 1 and is exposed. The arrangement unit 15x includes a transparent or translucent table (for example, a tray-like table such as a petri dish) on which an unpackaged and exposed medicine is placed. In addition, since there is no need to convey the continuous packaging bag 3 in the modification, a device corresponding to the conveyance unit 14 is not provided in the device main body 11x of the medicine verification device according to the modification.

FIG. 17 is a schematic view illustrating a device main body internal structure included in the device main body 11x of the medicine verification device according to the modification.

In the modification, images of the medicine on the arrangement unit 15x are captured by the cameras (that is, the first camera 16a and the second camera 16b) disposed above and below the arrangement unit 15x. At this time, each of the plurality of light emitting units 17a, 17b, 17c, and 17d disposed around the arrangement unit 15x is sequentially switched to emit light. Accordingly, also in the modification, an image of the verification target medicine disposed on the arrangement unit 15x is captured for each of light irradiation directions.

Thereafter, using similar procedure as in the above-described embodiment, the type and number of the medicines disposed on the arrangement unit 15x are verified, and then, whether the type and number of the medicines match prescription conditions (for example, details of the prescription presented at prescription to the patient who brought the verification target medicine) is verified. In a case where the type and number of medicines do not match the prescription conditions, verification is made as to whether the above-described first to fifth operation execution conditions are satisfied. In a case where any of the operation execution conditions is satisfied, the external force application unit 40 performs an external force applying operation. In the modification, a mechanism or the like that vibrates the platform provided as the arrangement unit 15x can be used as the external force application unit 40. After the external force applying operation is performed, the light irradiation direction is switched again to capture the image of the medicine on the arrangement unit 15x, and thereafter, the medicine verification is repeated in the procedure similar to the procedure described above.

As described above, in the modification, the verification is performed in a state where the unpackaged medicine is disposed on the arrangement unit 15x. Similarly to the above-described embodiment, it is also possible, in the modification, to perform external force applying operation when it is necessary to move the verification target medicine, leading to enhancement of accuracy and speed of the medicine verification. The medicine verification device according to the modification is not only used for the verification of a medicine in an unpackaged state, but also usable for the verification of a medicine contained in an individual packaging bag 1 (packaging bag 1 as a separate bag) which is not a continuous packaging bag 3.

Furthermore, while the above embodiment is an exemplary case where a plurality of medicines are packaged in the packaging bag 1 and these medicines (a plurality of medicines) are medicines to be a verification target medicine, the present invention is not limited to this case. The number of medicines packaged in the packaging bag 1 can be set to any number and may be only one, or may be two or more.

Furthermore, while the above embodiment is a case where the condition determination unit 26 verifies whether each of operation execution conditions is satisfied during the period between the conveyance operations of the conveyance unit 14 (that is, during the stop period of the conveyance operation), immediately after execution of verification flow by the verification unit 25, the present invention is not limited to this procedure. For example, it is also allowable to use a procedure in which the condition determination unit 26 determines whether the operation execution condition is satisfied at a stage before the execution of the verification flow by the verification unit 25, and the external force application unit 40 executes the external force applying operation at a time when the operation execution condition is satisfied.

What is claimed is:

1. A medicine verification device comprising:
   an arrangement unit on which a verification target medicine is disposed;
   an image capturing unit that captures an image of the verification target medicine disposed on the arrangement unit;
   a light irradiation unit that emits light to the verification target medicine disposed on the arrangement unit when the image capturing unit captures the image;
   a prescription condition information acquisition unit that acquires prescription condition information indicating a prescription condition set for prescribing a medicine;
   an external force application unit that executes an external force applying operation of applying an external force to the verification target medicine disposed on the arrangement unit to move the verification target medicine; and
   a control unit that causes the external force application unit to execute the external force applying operation when an operation execution condition is satisfied,
   wherein the operation execution condition includes at least one of:
   a first operation execution condition that the number of the verification target medicines appearing in the image differs from the quantity of the medicines specified from the prescription condition information; and
   a second operation execution condition that a shape of the verification target medicine appearing in the image differs from the shape corresponding to a type of the medicine specified from the prescription condition information, and
   the operation execution condition further includes:
   a third operation execution condition that a plurality of medicines are disposed on the arrangement unit as the verification target medicine and that one medicine and another medicine out of the plurality of medicines are adjacent to each other in an irradiation direction when the light irradiation unit performs light emission; and
   a fourth operation execution condition that an arrangement position, within the arrangement unit, of the verification target medicine appearing in the image is a position within a predetermined region;
   wherein the first operation execution condition is that the number of verification target medicines appearing in the image is smaller than the quantity of medicines specified from the prescription condition information;
   wherein the operation execution condition further includes a fifth operation execution condition that a posture of the verification target medicine appearing in the image is the posture that causes identification information formed on the verification target medicine to be outside an imaging range of the image capturing unit; and
   wherein the image capturing unit includes a plurality of cameras, and the fifth operation execution condition is that the posture of the verification target medicine appearing in the image is a posture that causes the identification information to be outside an imaging range of each of the plurality of cameras.

2. The medicine verification device according to claim 1, wherein the third operation execution condition is that the plurality of medicines are disposed on the arrangement unit and that the one medicine and the other medicine having a thickness greater than the one medicine are adjacent to each other in the irradiation direction in a state where the other medicine is disposed at a position that blocks light emitted from the light irradiation unit.

3. The medicine verification device according to claim 1, wherein the light irradiation unit has a plurality of light emitting units and emits light in different directions using the plurality of light emitting units, and
   when the third operation execution condition is satisfied, the control unit causes the external force application unit to execute the external force applying operation in a case where there exists at least one combination of the one medicine and the other medicine adjacent to each other in the irradiation direction.

4. The medicine verification device according to claim 1, wherein the region is a region separated from the light emitting unit of the light irradiation unit by a distance being a threshold or more in the light irradiation direction.

5. The medicine verification device according to claim 1, wherein, when the fifth operation execution condition is satisfied after causing the external force application unit to execute the external force applying operation, the control unit causes the external force application unit to repeatedly execute the external force applying operation.

6. The medicine verification device according to claim 1, wherein the verification target medicine is disposed on the arrangement unit in a state of being packed in a light-transmissive packaging bag.

7. The medicine verification device according to claim 6, further comprising:
   a conveyance unit that conveys a continuous packaging bag having a strip-like shape including continuously arranged packaging bags, along a conveyance path; and
   a condition determination unit that determines whether the operation execution condition is satisfied,
   wherein the arrangement unit is provided at an intermediate position of the conveyance path,
   the packaging bag in the continuous packaging bag disposed on the arrangement unit is switched by the conveyance of the continuous packaging bag by the conveyance unit, and
   the image capturing unit captures the image every time the packaging bag disposed on the arrangement unit is switched.

8. The medicine verification device according to claim 7, wherein, in a case that the condition determination unit has determined that the operation execution condition is satisfied, the control unit causes the external force application unit to execute the external force applying operation of applying an external force to the verification target medicine within the packaging bag disposed on the arrangement unit at a time when a result of the determination is obtained by the condition determination unit.

9. The medicine verification device according to claim 1, wherein the verification target medicine is disposed in an unpackaged and exposed state on the arrangement unit.

10. The medicine verification device according to claim 1, further comprising a verification unit that verifies type and the number of the verification target medicines.

11. The medicine verification device according to claim 10,
wherein the verification unit reads a master image pre-registered for the type of medicine specified from the prescription condition information and verifies the type of the verification target medicine by using the image captured by the image capturing unit and the master image, and
the operation execution condition includes the second operation execution condition, in which the second operation execution condition is that the shape of the verification target medicine appearing in the image captured by the image capturing unit differs from the shape of the medicine appearing in the master image.

12. The medicine verification device according to claim 1, wherein the external force application unit applies any one of vibration, swing, impact, and pressing force to the verification target medicine disposed on the arrangement unit, as the external force.

13. A medicine verification method comprising:
disposing a verification target medicine on an arrangement unit;
capturing an image of the verification target medicine disposed on the arrangement unit;
emitting light, using a light irradiation unit, to the verification target medicine disposed on the arrangement unit when the image is captured;
acquiring prescription condition information indicating a prescription condition set for prescribing a medicine;
causing an external force application unit to execute an external force applying operation of applying an external force to the verification target medicine disposed on the arrangement unit to move the verification target medicine when an operation execution condition is satisfied, wherein the operation execution condition includes at least one of:
a first operation execution condition that the number of the verification target medicines appearing in the image differs from the quantity of the medicines specified from the prescription condition information; and
a second operation execution condition that a shape of the verification target medicine appearing in the image differs from a shape corresponding to a type of the medicine specified from the prescription condition information, and
the operation execution condition further includes:
a third operation execution condition that a plurality of medicines are disposed on the arrangement unit as the verification target medicine and that one medicine and another medicine out of the plurality of medicines are adjacent to each other in an irradiation direction when the light irradiation unit performs light emission; and
a fourth operation execution condition that an arrangement position, within the arrangement unit, of the verification target medicine in the image is a position within a predetermined region;
wherein the first operation execution condition is that the number of verification target medicines appearing in the image is smaller than the quantity of medicines specified from the prescription condition information;
wherein the operation execution condition further includes a fifth operation execution condition that a posture of the verification target medicine appearing in the image is the posture that causes identification information formed on the verification target medicine to be outside an imaging range of the image capturing unit; and
wherein the image capturing unit includes a plurality of cameras, and the fifth operation execution condition is that the posture of the verification target medicine appearing in the image is a posture that causes the identification information to be outside an imaging range of each of the plurality of cameras.

14. The medicine verification device according to claim 1, wherein the light irradiation unit has a plurality of light emitting units and emits light in different directions using the plurality of light emitting units, and when the third operation execution condition is satisfied, the control unit causes the external force application unit to execute the external force applying operation in a case where there exists at least one combination of the one medicine and the other medicine adjacent to each other in the irradiation direction.

15. The medicine verification device according to claim 2, wherein the light irradiation unit has a plurality of light emitting units and emits light in different directions using the plurality of light emitting units, and
when the third operation execution condition is satisfied, the control unit causes the external force application unit to execute the external force applying operation in a case where there exists at least one combination of the one medicine and the other medicine adjacent to each other in the irradiation direction.

16. The medicine verification device according to claim 1, wherein, when the fifth operation execution condition is satisfied after causing the external force application unit to execute the external force applying operation, the control unit causes the external force application unit to repeatedly execute the external force applying operation.

* * * * *